(12) United States Patent
Lyons

(10) Patent No.: US 12,383,362 B2
(45) Date of Patent: Aug. 12, 2025

(54) METHOD AND APPARATUS FOR SUPPORTING SURGICAL INSTRUMENTS

(71) Applicant: Dieble Surgical LLC, North Lawrence, OH (US)

(72) Inventor: Diane Lyons, North Lawrence, OH (US)

(73) Assignee: Dieble Surgical LLC, North Lawrence, OH (US)

( * ) Notice: Subject to any disclaimer, the term of this patent is extended or adjusted under 35 U.S.C. 154(b) by 0 days.

(21) Appl. No.: 18/505,249

(22) Filed: Nov. 9, 2023

(65) Prior Publication Data
US 2025/0152290 A1   May 15, 2025

(51) Int. Cl.
*A61B 50/24* (2016.01)

(52) U.S. Cl.
CPC .................. *A61B 50/24* (2016.02)

(58) Field of Classification Search
CPC ......... A61B 50/24; A61B 50/22; A61B 50/20; A61B 50/26; A61B 50/33
USPC ............... 211/85.13; 422/300, 301; 206/370; D24/227, 229
See application file for complete search history.

(56) References Cited

U.S. PATENT DOCUMENTS

| | | | | |
|---|---|---|---|---|
| 1,733,487 A * | 10/1929 | Hackley | ................. | A47B 61/04 211/35 |
| 2,134,606 A * | 10/1938 | Hackworth | .......... | A47B 57/583 108/27 |
| 2,620,929 A * | 12/1952 | Sportsman | ............. | A47B 65/15 211/69.5 |
| 2,903,129 A * | 9/1959 | Anderson, III | ........ | A61B 50/33 206/363 |
| 3,438,506 A * | 4/1969 | Groth | ........................ | A47F 5/01 211/70.6 |
| 3,564,662 A * | 2/1971 | Dold | ...................... | A61B 50/10 206/370 |
| 3,888,353 A * | 6/1975 | Leifheit | ................. | A47B 61/04 211/37 |
| 3,925,014 A * | 12/1975 | Langdon | ................... | A61L 2/26 206/370 |
| 4,229,420 A * | 10/1980 | Smith | .................... | A61B 50/22 606/1 |

(Continued)

FOREIGN PATENT DOCUMENTS

WO   2008008399   1/2008

*Primary Examiner* — Jennifer E. Novosad
(74) *Attorney, Agent, or Firm* — Sand, Sebolt & Wernow Co., LPA

(57) ABSTRACT

A surgical instrument stand apparatus for supporting and organizing surgical instruments. Apparatus includes a first foot, a second foot, a support tube that extends between the first foot and the second foot and holds the first and second feet at a fixed distance from one another by the support tube, and at least one stand accessory that is selectively operably engageable with the first foot and the second foot for supporting at least one set of surgical instruments. When the at least one set of surgical instruments is supported by the support tube and the at least one stand accessory, the at least one stand accessory is engaged with the first and second feet at first positions. Apparatus may also include at least another stand accessory that is selectively operably engageable with the first and second feet at second positions to support another set of surgical instruments.

9 Claims, 24 Drawing Sheets

(56) References Cited

U.S. PATENT DOCUMENTS

| | | | | |
|---|---|---|---|---|
| 4,342,391 | A | * | 8/1982 | Schainholz ............ A61B 50/20 206/370 |
| 4,577,755 | A | * | 3/1986 | Ramsay ................... A61L 2/26 206/370 |
| 4,854,456 | A | * | 8/1989 | Lee ...................... A47B 81/007 211/175 |
| 4,865,821 | A | * | 9/1989 | Langdon ................ A61B 50/22 422/561 |
| 5,137,151 | A | * | 8/1992 | Choate .................. A61B 50/20 206/370 |
| 5,228,578 | A | * | 7/1993 | Wu ........................ A47B 65/20 211/175 |
| 5,435,295 | A | * | 7/1995 | Gerrard .................. F24B 1/193 126/541 |
| 5,449,069 | A | * | 9/1995 | Pijanowski ............ A61B 50/20 206/370 |
| 5,451,380 | A | * | 9/1995 | Zinnanti ................ A61B 50/20 206/370 |
| D368,532 | S | * | 4/1996 | Jonkman ...................... D24/227 |
| 5,759,502 | A | * | 6/1998 | Spencer .................... A61L 2/26 206/370 |
| 5,992,647 | A | * | 11/1999 | Malik ................ G11B 23/0236 211/40 |
| 6,230,888 | B1 | * | 5/2001 | Frieze .................... A61B 50/22 206/370 |
| 6,534,000 | B1 | * | 3/2003 | Michaelson ............... A61L 2/26 422/26 |
| 6,648,150 | B2 | * | 11/2003 | Hartstone .......... G11B 33/0461 211/11 |
| 7,150,364 | B2 | * | 12/2006 | Jablow ................... A47B 45/00 211/175 |
| 7,461,751 | B2 | * | 12/2008 | Lyons .................... A61B 50/13 211/85.13 |
| 7,871,581 | B1 | * | 1/2011 | Coleman ................ A61B 50/20 211/85.13 |
| 8,083,059 | B1 | * | 12/2011 | Wessel, IV ............ B25H 3/003 206/378 |
| 8,641,984 | B2 | * | 2/2014 | Alston ................... A61B 50/30 206/370 |
| 9,259,272 | B2 | * | 2/2016 | Ramkhelawan .......... B65B 5/08 |
| 12,048,570 | B2 | * | 7/2024 | Henke .................... A61B 50/22 |
| 2009/0152414 | A1 | * | 6/2009 | Lyons .................... A61B 50/24 248/176.1 |
| 2012/0234781 | A1 | * | 9/2012 | Cogliano ................ B25H 3/06 211/85.13 |
| 2016/0143702 | A1 | * | 5/2016 | Ramkhelawan ....... A61B 50/20 206/370 |

* cited by examiner

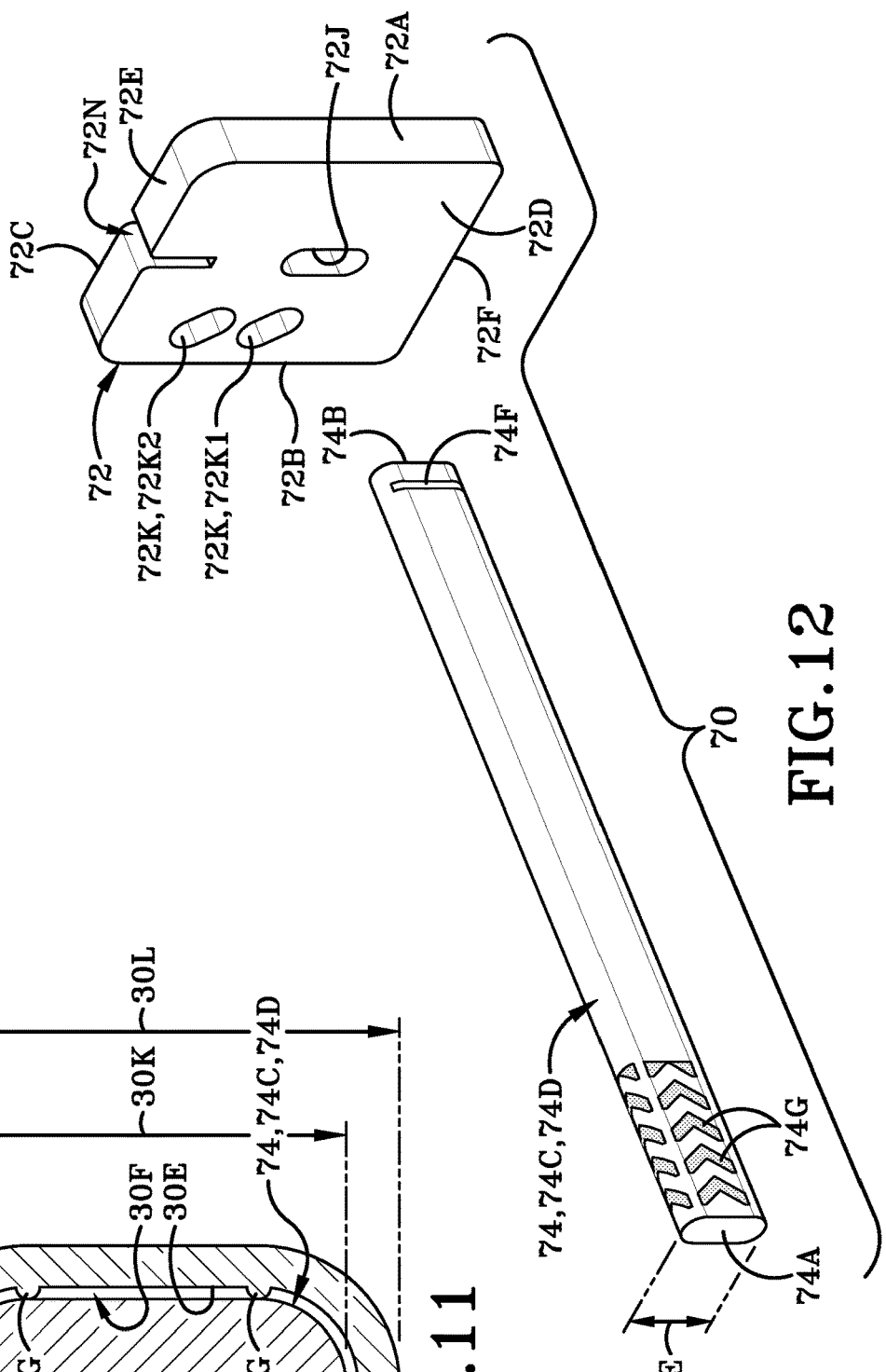

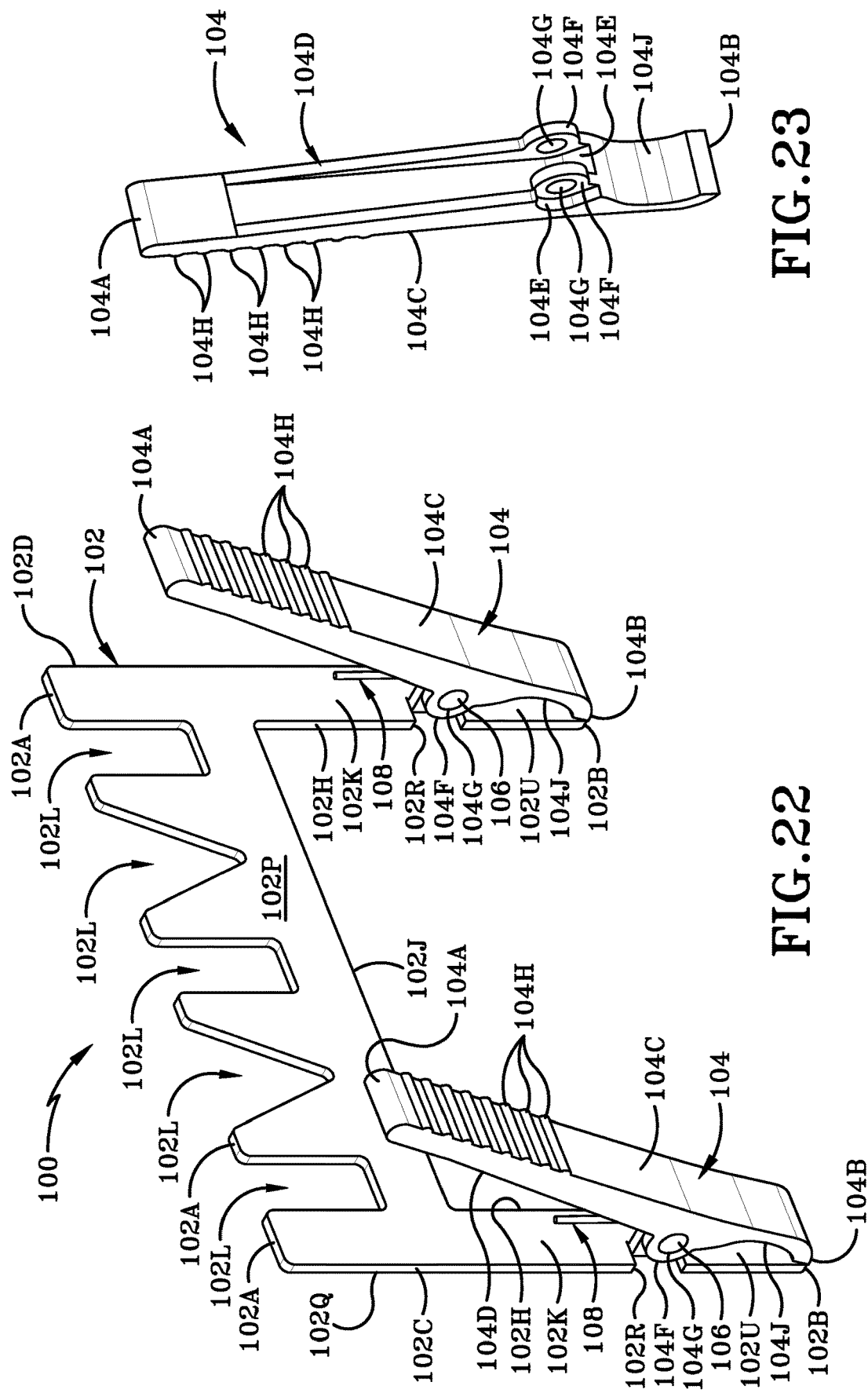

METHOD AND APPARATUS FOR SUPPORTING SURGICAL INSTRUMENTS

TECHNICAL FIELD

This disclosure is directed to a surgical instrument stand apparatus for supporting at least one or more types of surgical instruments for surgical or medical procedures.

BACKGROUND ART

Surgical instruments that may be needed during a surgical procedure are conventionally assembled in advance of the surgery on a tray by, for example, a surgery technician or nurse. The tray is stably supported, such as along one side thereof, on rollers above the surgery floor in order to allow mobility and accessibility to the surgical instruments. The height of the tray above the surgery floor is such as to permit the tray to be selectively positioned at will over any portion of an occupied surgery bed, within easy reach of medical personnel. The tray, in combination with the support and rollers therefor, is conventionally referred to as a "mayo stand."

Various types of surgical instruments are routinely loaded onto a mayo stand in preparation for use in surgery. These surgical instruments are generally arranged on the mayo stand in a nesting, parallel relationship with the handles of the surgical instruments in alignment. In many cases, similar types of surgical instruments are grouped together and graded by size. Such a lineup of surgical instruments is commonly known or referred to as a "stringer" or "stringer of surgical instruments." Examples of surgical instruments that would commonly be included in a stringer on a mayo stand include hemostats, tonsils, Haney clamps, and needle holders.

However, these types of arrangements on medical stands or mayo stands pose issues to medical personal during surgical or medical procedures. In one instance, surgical instruments that are provided on rolled towels during surgical procedures tend to lean over on these rolled towels which create a greater footprint and/or space on medical stands making it difficult to retrieve or return instruments due to the close proximity of these surgical instruments. In this same instance, the greater footprint and/or space created by the surgical instruments may make retrieving and returning surgical instruments be more difficult or problematic when a specific surgical procedure becomes fast paced. While such retrieval and return issues may be minimal at times, continuous issues of retrieving and returning various types of surgical instruments during a surgical procedure may increase the time of surgery, unnecessary stress and anxiety placed on medical staff during surgery, and potential errors or mistakes in retrieving a desired surgical instrument.

SUMMARY OF THE INVENTION

The presently disclosed surgical instrument stand apparatus accomplishes issues in supporting at least one or more types of surgical instruments for surgical or medical procedures. In one aspect, the surgical instrument stand apparatus includes at least one or a first stand accessory for supporting at least one set of surgical instruments when transporting the surgical instrument stand and the at least one set of surgical instruments. In another aspect, the surgical instrument stand apparatus includes at least another or a second stand accessory for supporting and organizing at least another set of surgical instruments during a surgical or medical procedure. In yet another aspect, the surgical instrument stand apparatus includes at least one expansion assembly that expands and/or extends the overall footprint of the surgical instrument stand apparatus for supporting additional surgical instruments. The presently disclosed surgical instrument stand apparatus addresses inadequacies of known surgical instrument stand apparatuses and devices.

In one aspect, an exemplary embodiment of the present disclosure may provide a surgical instrument stand apparatus. The apparatus includes a first foot, a second foot, and a support tube that extends between the first foot and the second foot, wherein the first foot and the second foot are held at a fixed distance from one another by the support tube. The apparatus also includes at least one stand accessory that is selectively operably engageable with the first foot and the second foot for supporting at least one set of surgical instruments.

This exemplary embodiment or another exemplary embodiment may further include that when the at least one set of surgical instruments is supported by the support tube and the at least one stand accessory, the at least one stand accessory is engaged with the first foot and the second foot at first positions. This exemplary embodiment or another exemplary embodiment may further include that each of the first foot and the second foot comprises: an outer side; an inner side facing in an opposite direction relative to the outer side; a central opening extending between the outer side and the inner side and configured to receive the support tube; and at least two accessory openings extending between the outer side and the inner side and being offset from the central opening; wherein one or both of the at least two accessory openings are configured to receive the at least one stand accessory. This exemplary embodiment or another exemplary embodiment may further include at least another stand accessory selectively operably engageable with the first foot and the second foot at second positions different than the first positions, wherein at least another set of surgical instruments is supported by the at least another stand accessory. This exemplary embodiment or another exemplary embodiment may further include that each of the first foot and the second foot further comprises: a bottom end that is configured to engage with a support surface; and a top end that is vertically opposite to the bottom end and is free from engaging the support surface; wherein the at least another stand accessory is configured to selectively operably engage with the top end of each of the first foot and the second foot. This exemplary embodiment or another exemplary embodiment may further include that the first foot further comprises: a first slit extending downwardly into the first foot from the top end towards the bottom end, wherein the first slit is configured to receive a first end of the at least another stand accessory; and a second slit extending downwardly into the second foot from the top end towards the bottom end and being coaxial with the first slit of the first foot, wherein the second slit is configured to receive a second end of the at least another stand accessory that is opposite to the first end of the at least another stand accessory. This exemplary embodiment or another exemplary embodiment may further include that the support tube comprises: a first end that operably engages with the first foot; a second end that is longitudinally opposite to the first end and operably engages with the second foot; and a wall extending between the first end and the second end and defining a passageway therethrough with an inner diameter. This exemplary embodiment or another exemplary embodiment may further include that the support tube further comprises: at least one opening defined in the wall between the first end of the support tube and the second end of the support tube; wherein the at least one opening provides fluid communication between the passageway of the support tube and an external environment that surrounds the support tube. This exemplary embodiment or another exemplary embodiment may further include an expansion assembly selectively operably engagable with the support tube at one of the first end of the support tube and the second end of the support tube. This exemplary embodiment or another exemplary embodiment may further include that the expansion assembly comprises: an expansion foot; and an expansion support bar extending between the expansion foot and one of the first foot and the second foot. This exemplary embodiment or another exemplary embodiment may further include that the expansion support bar comprises: a first end that operably engages with the expansion foot; a second end that is longitudinally opposite to the first end and is configured to selectively operably engage with the support tube at one of the first end of the support tube and the second end of the support tube; and a wall extending between the first end and the second end and defining an outer diameter that is less than the inner diameter of the support tube; wherein the expansion support bar is slidably moveably inside of the passageway of the support tube. This exemplary embodiment or another exemplary embodiment may further include that the expansion foot comprises: a bottom expansion end that is configured to engage with a support surface; a top end that is vertically opposite to the bottom end and is free from engaging the support surface; and an expansion slit extending downwardly into the expansion foot from the top expansion end towards the bottom expansion end and is coaxial with a first slit defined in the first foot and a second slit defined in the second foot; wherein at least another stand accessory is configured to selectively operably engage with the top end of the expansion foot inside of the expansion slit remote from the expansion support bar. This exemplary embodiment or another exemplary embodiment may further include that the at least another stand accessory comprises: at least one set of recesses defined in the at least another stand accessory; wherein the at least another set of surgical instruments is held by the at least another stand accessory inside the at least one set of recesses. This exemplary embodiment or another exemplary embodiment may further include at least one clip that is selectively operably engageable with the support tube; wherein the at least one clip is selectively positionable along the support tube between the first foot and the second foot, wherein the at least one clip is configured to separate one surgical instrument of the at least one set of surgical instruments from another surgical instrument of the at least one set of surgical instruments, and wherein the at least one clip is operative to hold a surgical instrument of the at least one set of surgical instruments in operative engagement with the support tube in a desired orientation. This exemplary embodiment or another exemplary embodiment may further include at least another stand accessory selectively operably engageable with the support tube between the first foot and the second foot, wherein at least another set of surgical instruments is supported by the at least another stand accessory inside at least one set of recesses defined in the at least another stand accessory. This exemplary embodiment or another exemplary embodiment may further include at least another stand accessory selectively operably engageable with the support tube between the first foot and the second foot, wherein at least another set of surgical instruments is supported by the at least another stand accessory remote from the support tube. This exemplary embodiment or another exemplary embodiment may further include that the at least another stand accessory further comprises: a plate; and a pair of clips that pivotably engage with the plate; wherein the plate and the pair of clips cooperatively engage with the support tube between the first foot and the second foot. This exemplary embodiment or another exemplary embodiment may further include the at least another stand accessory further comprises: at least one set of recesses defined in the plate; wherein the at least another set of surgical instruments is supported by the plate inside of the at least one set of recesses.

In another aspect, an exemplary embodiment of the present disclosure may provide a method of supporting at least one set of surgical instruments with a surgical instrument stand apparatus. The method comprises steps of engaging a first foot of the surgical instrument stand apparatus with a first end of a support tube of the surgical instrument stand apparatus; engaging a second foot of the surgical instrument stand apparatus with a second end of the support tube, wherein the second foot is spaced apart from the first foot at a fixed distance defined by the support tube; selecting between a first stand accessory and a second stand accessory; engaging the selected first stand accessory or the second stand accessory with the first foot and the second foot; and supporting at least one set of surgical instruments with the surgical instrument stand apparatus by the support tube and the selected first stand accessory or the selected second stand accessory.

This exemplary embodiment or another exemplary embodiment may further include that when the first stand accessory is selected, the method further comprises: inserting a first end of the first stand accessory through the first foot, the second foot, and first handles of the at least one set of surgical instruments; engaging the first stand accessory with the first foot, the second foot, and the first handles of the at least one set of surgical instruments; inserting a second end of the first stand accessory through second handles of the at least one set of surgical instruments; and engaging the first stand accessory with the second handles of the at least one set of surgical instruments. This exemplary embodiment or another exemplary embodiment may further include steps of clamping at least one clip with the support tube; and separating the at least one set of surgical instruments into at least two groups. This exemplary embodiment or another exemplary embodiment may further include that when the second stand accessory is selected in the step of selecting between the first stand accessory and the second stand accessory, the method further comprises: engaging a first end of the second stand accessory with the first foot inside a first slit defined in the first foot; and engaging a second end of the second stand accessory with the second foot inside a second slit defined in the second foot; wherein the second stand accessory is positioned above and spaced apart from the support tube. This exemplary embodiment or another exemplary embodiment may further include a step of engaging at least one expansion assembly with the support tube at one or both of the first end of the support tube and the second end of the support tube. This exemplary embodiment or another exemplary embodiment may further include that when the second stand accessory is selected in the step of selecting between the first stand accessory and the second stand accessory, the method further comprises: engaging a first end of the second stand accessory with one of the first foot inside a first slit defined in the first foot and the second foot inside a second slit defined in the second foot; and engaging a second end of the second stand accessory with an expansion foot of the expansion assembly inside an expansion slit defined in the expansion foot; wherein the second stand accessory is positioned above and spaced apart from the support tube and an expansion support bar of the expansion assembly.

BRIEF DESCRIPTION OF THE DRAWINGS

Sample embodiments of the present disclosure are set forth in the following description, are shown in the drawings and are particularly and distinctly pointed out and set forth in the appended claims.

FIG. 11 (FIG. 11) is a cross-sectional view of the support tube of the surgical instrument stand apparatus and an expansion support of the expansion assembly taken in the direction of line 11-11 as shown in FIG. 10; wherein the expansion support engages with the support tube inside of the support tube.

FIG. 12 (FIG. 12) is an exploded view of the expansion assembly shown in FIG. 10.

FIG. 22 (FIG. 22) is a front, top, first side isometric perspective view of the clamping rack shown in FIG. 21.

FIG. 23 (FIG. 23) is a rear, top, second side isometric perspective view of a clip of the clamping rack shown in FIG. 21.

Similar numbers refer to similar parts throughout the drawings.

DETAILED DESCRIPTION

FIGS. 1-7 illustrate a first embodiment or configuration of a surgical instrument stand apparatus (hereinafter "stand") generally referred to as 1. As illustrated in FIGS. 1-7, stand 1 is configured to support and organize at least one set of surgical instruments that is selected by medical professions for a particular surgical procedure or medical procedure. It should be understood that stand 1 assists medical professions in organizing and arranging various types of surgical instruments along the stand 1 for easily transporting these surgical instruments from a preparation station to a surgical or operating room or to select a desired surgical instrument during a surgical procedure. The components and devices that form the stand 1 are now discussed in greater detail below.

Figure 4:
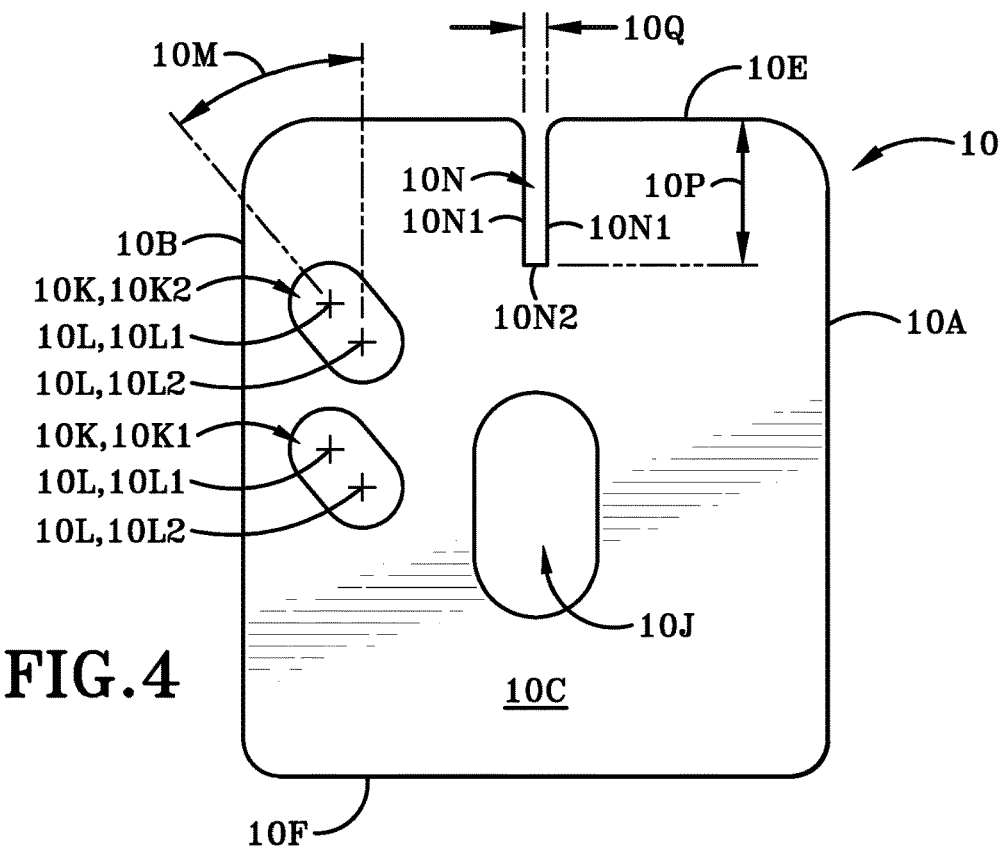
FIG. 4 (FIG. 4) is a first side elevation view of a first foot of the surgical instrument stand apparatus shown in FIG. 1.
Figure 5:
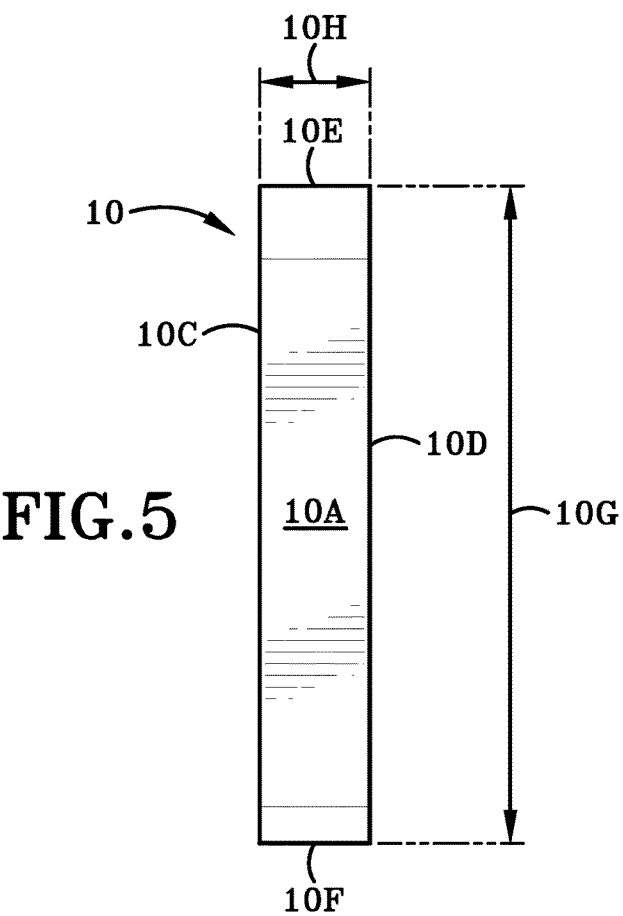
FIG. 5 (FIG. 6) is a front elevation view of the first foot of the surgical instrument stand apparatus shown in FIG. 1.

Stand 1 includes a first foot or upright support 10. As best seen in FIGS. 4-5, the first foot 10 includes a first or front end 10A, a second or rear end 10B longitudinally opposite to the front end 10A, and a longitudinal direction defined therebetween. As best seen in FIG. 5, first foot 10 also includes a first or outer side 10C that extends between the front end 10A and the rear end 10B, a second or inner side 10D that extends between the front end 10A and the rear end 10B and is transversely opposite to the outer side 10C, and a transverse direction defined therebetween. As best seen in FIGS. 4-5, first foot 10 also includes a top end 10E that is positioned above the front end 10A, the rear end 10B, the outer side 10C, and the inner side 10D, a bottom end 10F that is positioned below the front end 10A, the rear end 10B, the outer side 10C, and the inner side 10D and is vertically opposite to the top end 10E, and a vertical direction defined between. First foot 10 also defines an overall height 10G that is measured between the top end 10E and the bottom end 10F (see FIG. 5). First foot 10 also defines an overall width 10H that is measured between the outer side 10C and the inner side 10D and is less than the overall height 10G in the present disclosure (see FIG. 5). In other exemplary embodiments, first foot 10 may define any suitable heights, widths, or lengths dictated by the implementation of the stand 1 in surgical and/or medical procedures.

Still referring to first foot 10, first foot 10 also defines a central opening 10J. As best seen in FIG. 4, the central opening 10J extends entirely through the first foot 10 along the transverse direction of the first foot 10 between the outer side 10C and the inner side 10D. In the present disclosure, the outer side 10C and the inner side 10D are in operative communication with one another at the central opening 10J. In the present disclosure, the central opening 10J is also an oblong-shaped or oval-shaped opening that is configured to receive an end of a support tube of the stand 1 to engage the first foot 10 and the support tube with one another, which is discussed in greater detail below. In other exemplary embodiment, central opening 10J may define any suitable shape that is configured to receive an end of a support tube of the stand 1 to engage the first foot 10 and the support tube with one another.

Still referring to first foot 10, first foot 10 also defines a pair of accessory openings 10K. As best seen in FIG. 4, each accessory opening of the pair of accessory openings 10K extends entirely through the first foot 10 along the transverse direction of the first foot 10 between the outer side 10C and the inner side 10D. In the present disclosure, the outer side 10C and the inner side 10D are in operative communication with one another at each accessory opening of the pair of accessory openings 10K. The pair of accessory openings 10K is also spaced apart and offset from the central opening 10J and defined proximate to the rear end 10B of first foot 10. In the present disclosure, a first accessory opening 10K1 of the pair of the accessory openings 10K is defined below a second accessory opening 10K2 of the pair of the accessory openings 10K.

Each accessory opening of the pair of accessory openings 10K also defines a pair of axes 10L that is parallel with the transverse direction of the first foot 10. Upon assembly, an instrument stringer or first stand accessory of the stand 1 may lie on one of axes of the pair of axes 10L for supporting and organizing surgical instruments along the length of the stand 1, which are discussed in greater detail below. Each axis of the pair of axes 10L is also offset from one another and defined at an angle 10M measured between a first axis 10L1 of the pair of axes 10L and a second axis 10L2 of the pair of axes 10L. In the present disclosure, the angle 10M measured between the pair of axes 10L is an acute angle. With such configuration, each accessory opening of the pair of accessory opening 10K is also angled and/or slanted based on the angle 10M measured between the pair of axes 10L extending through each accessory opening of the pair of accessory opening 10K.

In the present disclosure, each accessory opening of the pair of accessory openings 10K is an oblong-shaped or oval-shaped opening that is configured to receive an instrument stringer or first stand accessory of the stand 1 for supporting and organizing surgical instruments along the length of the stand 1, which are discussed in greater detail below. In other exemplary embodiment, each accessory opening of the pair of accessory openings 10K may define any suitable shape that is configured to receive an instrument stringer or first stand accessory of the stand 1 for supporting and organizing surgical instruments along the length of the stand 1.

While first foot 10 defines the pair of accessory openings 10K, a first foot or any foot discussed and illustrated herein may define any suitable number of accessory openings as dictated by the implementation of the accessory openings, including the number of instrument stringers or first stand accessories that are intended to be received by a first foot or any foot of a stand mentioned herein. Examples of suitable numbers of accessory openings defined in a first foot or any foot discussed and illustrated herein include at least one, two, a plurality, three, four, five, and other suitable numbers of accessory openings that may be defined in a foot discussed and illustrated herein. In one exemplary embodiment, a first set of accessory openings may be defined at a front end of a foot, and a second set of accessory openings may be defined at a rear end of the foot opposite to the first set of accessory openings.

Still referring to first foot 10, first foot 10 also defines a first slit 10N. As best in FIG. 4, the first slit 10N is defined by a pair of interior vertical walls 10N1 that extends vertically downward into the first foot 10 from the top end 10E to an interior base wall 10N2. The first slit 10N also defines a slit height 10P that is measured along the lengths of the pair of interior vertical walls 10N1 from the top end 10E to the interior base wall 10N2. The first slit 10N also defines a slit width 10Q that is measured between the pair of interior vertical walls 10N1. Such use of the first slit 10N is discussed in greater detail below.

Stand 1 also includes a second foot 20. In the present disclosure, the first foot 10 and the second foot 20 are identical to one another for stand 1. As such, a front end 20A, a rear end 20B, an outer side 20C, an inner side 20D, a top end 20E, a bottom end 20F, a central opening 20J, a pair of accessory openings 20K, and a second slit 20N defined by a pair of internal vertical walls 20N1 and an internal base wall 20N2 of the second foot 20 are identical to the front end 10A, rear end 10B, outer side 10C, inner side 10D, top end 10E, bottom end 10F, central opening 10J, pair of accessory openings 10K, and the first slit 10N defined by the pair of internal vertical walls 10N1 and the internal base wall 10N2 of the first foot 10. It should be understood that, while not illustrated herein, the overall height 10G and the overall width 10H of the first foot 10 applies equally to an overall height and overall width of the second foot 20. It should also be understood that, while not illustrated herein, the pair of axes 10L and the angle 10M of the pair of accessory openings 10K of the first foot 10 applies equally to the pair of accessory openings 20K of the second foot 20. It should also be understood that, while not illustrated herein, the interior vertical walls 10N1 and the internal base wall 10N2 that define the first slit 10N having the slit height 10P and the slit width 10Q applies equally to the second slit 20N of the second foot 20.

While second foot 20 defines the pair of accessory openings 20K, a second foot or any foot discussed and illustrated herein may define any suitable number of accessory openings as dictated by the implementation of the accessory openings, including the number of instrument stringers or first stand accessories that are intended to be received by a second foot or any foot of a stand mentioned herein. Examples of suitable numbers of accessory openings defined in a second foot or any foot discussed and illustrated herein include at least one, two, a plurality, three, four, five, and other suitable numbers of accessory openings that may be defined in a foot discussed and illustrated herein. In one exemplary embodiment, a first set of accessory openings may be defined at a front end of a foot, and a second set of accessory openings may be defined at a rear end of the foot opposite to the first set of accessory openings.

Figure 3:
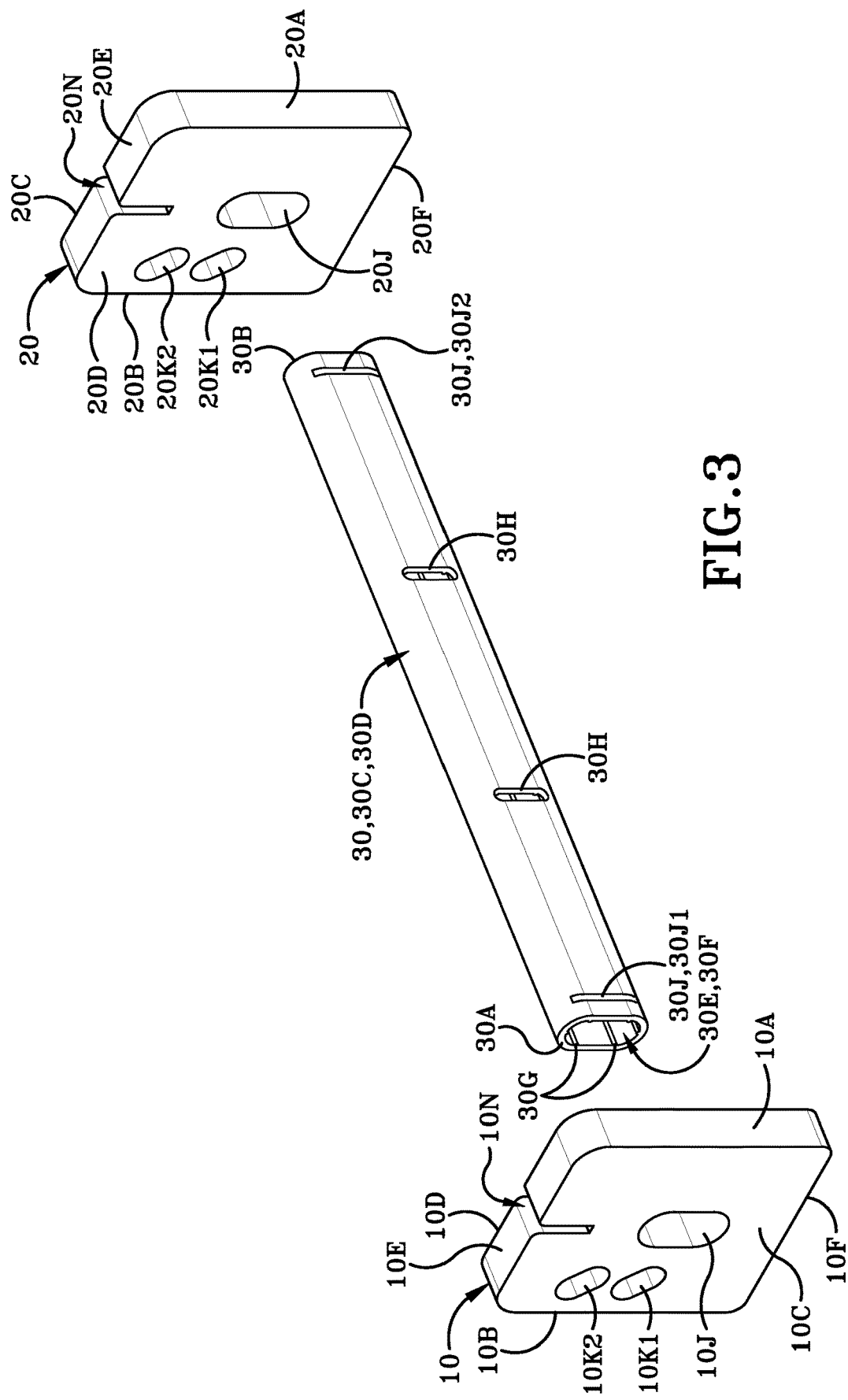
FIG. 3 (FIG. 3) is an exploded view of the surgical instrument stand apparatus shown in FIG. 1.

Stand 1 also includes a support tube 30 that operably engages with the first foot 10 and the second foot 20. As best seen in FIG. 3, the support tube 30 includes a first end 30A, a second end 30B that is longitudinally opposite to the first end 30A, a wall 30C that extends longitudinally between the first end 30A and the second end 30B, and a longitudinal direction defined therebetween. The support tube 30 also includes an exterior surface 30D that extends along the entire length of the wall 30C between the first end 30A and the second end 30B. The support tube 30 also includes an interior surface 30E that extends along the entire length of the wall 30C between the first end 30A and the second end 30B and faces in an opposite direction relative to the exterior surface 30D.

Still referring to support tube 30, support tube 30 also defines a passageway 30F. As best seen in FIGS. 3 and 11, the passageway 30F extends between the first end 30A and the second end 30B along the interior surface 30E of the support tube 30. The passageway 30F is also accessible at the first end 30A and the second end 30B since the first end 30A and the second end 30B are open ends. Support tube 30 also includes a set of internal ridges 30G that extends outwardly from the interior surface 30E and into the passageway 30F. In the present disclosure, each interior ridge of the set of internal ridges 30G also runs along the entire length of the support tube 30 between the first end 30A and the second end 30B; such use and purpose of the set of internal ridges 30G is discussed in greater detail below.

Still referring to support tube 30, support tube 30 also defines a set of apertures 30H. As best seen in FIG. 3, each aperture of the set of apertures 30H extends through the wall 30C from the exterior surface 30D to the interior surface 30E; the exterior surface 30D and the interior surface 30E are in operative communication with one another at each aperture of the set of apertures 30H. Each aperture of the set of apertures 30H also provides fluid communication between the passageway 30F of the support tube 30 and the exterior environment that surrounds the support tube 30. Such communication between the passageway 30F of the support tube 30 and the exterior environment may provide various uses for stand 1, including sterilizing the interior spaces of support tube 30 after being used in a surgical procedure, viewing a position of an expansion bar of an expansion assembly inside of the support tube 30, and other various uses that will be discussed in greater detail below.

In the present disclosure, the support tube 30 defines two apertures 30H. While support tube 30 defines two apertures 30H, a support tube discussed and illustrated herein may define any suitable number of apertures as dictated by the implementation of the accessory openings, including the number of apertures to allow sterilization and/or cleaning solution to enter into interior spaces of support tube 30 after being used in a surgical procedure, positions to view an expansion bar of an expansion assembly inside of the support tube 30, and other various uses. Examples of suitable numbers of apertures defined in a support tube include at least one, two, a plurality, three, four, five, and other suitable numbers of apertures that may be defined in a support tube discussed and illustrated herein.

Still referring to support tube 30, support tube 30 may also include a set of projections 30J. As best seen in FIG. 3, a first projection 30J1 of the set of projections 30J is defined at the first end 30A of the support tube 30, and a second projection 30J2 of the set of projections 30J is defined at the second end 30B of the support tube 30 opposite to the first projection 30J1. Such inclusion of the set of projections 30J may provide attachment means between the first foot 10 and support tube 30 when assembled with one another and between the second foot 20 and support tube 30 when assembled with one another. Stated differently, support tube 30 frictionally fits with the first foot 10 and with the second foot 20 due to the set of projections 30J pressing against an interior wall defined inside each central opening 10J, 20K of the first foot 10 and the second foot 20.

Figure 2:
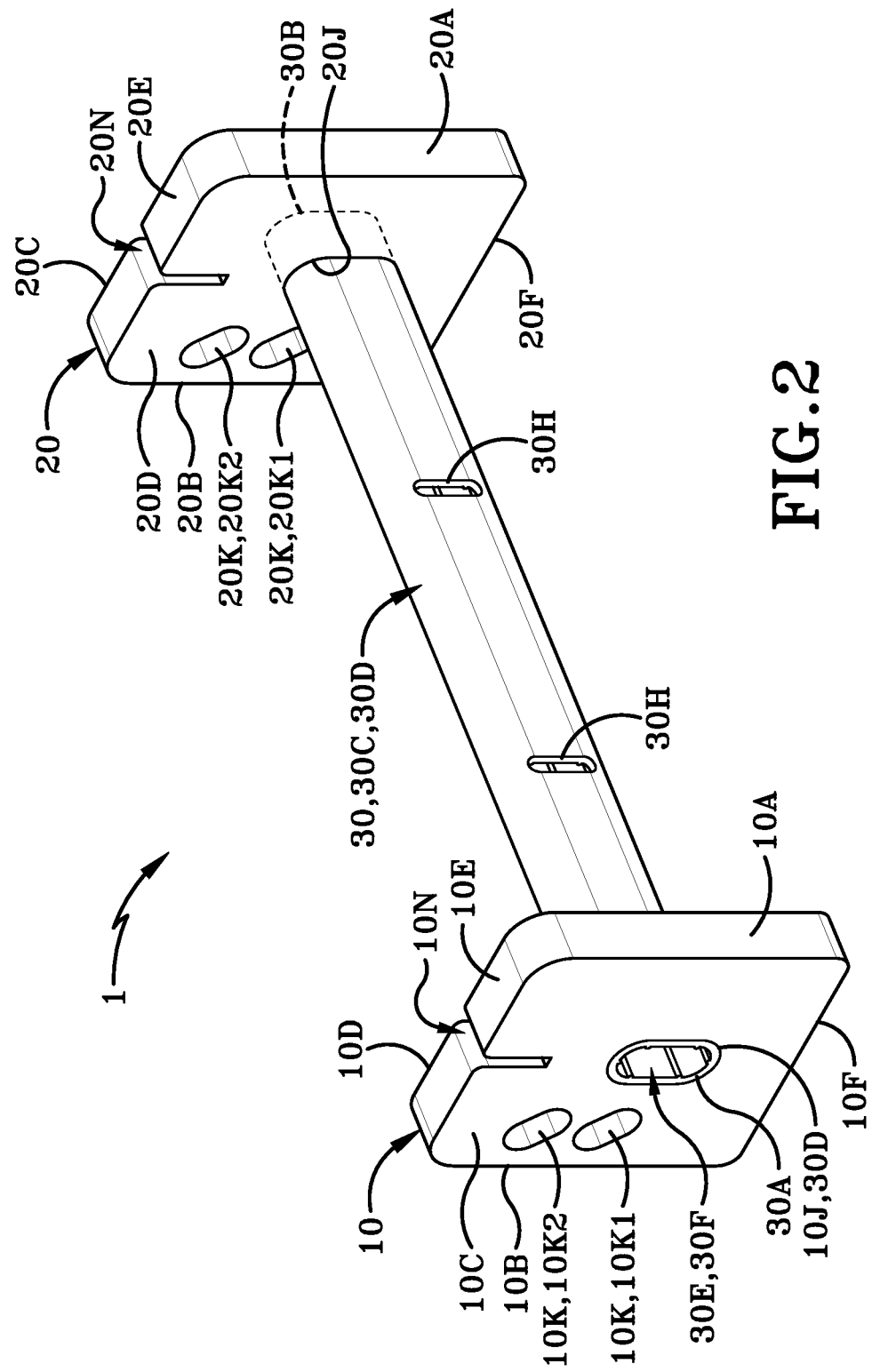
FIG. 2 (FIG. 2) is a front, top, first side isometric perspective view of the surgical instrument stand apparatus shown in FIG. 1.

Still referring to support tube 30, support tube 30 may also define an inner diameter 30K and an outer diameter 30L As best seen in FIG. 11, the inner diameter 30K of the support tube 30 is measured along the set of internal ridges 30G and is continuous from the first end 30A to the second end 30B. Referring to FIG. 3, the outer diameter 30L of the support tube 30 is also continuous along the support tube 30 from the first end 30A to the second end 30B. As best seen in FIG. 2, the outer diameter 30L is less than an inner diameter of the central opening 10J of the first foot 10 and an inner diameter of the central opening 20J of the second foot 20 so that support tube 30 is received by and engages with the first foot 10 and the second foot 20.

It should be understood that the support tube 30 may define any suitable length necessary for transporting and organizing surgical and/or medical equipment. In one exemplary embodiment, a length of a support tube discussed herein may be approximately six inches long when measured between a first end of the support tube and a second end of the support tube. In another exemplary embodiment, another length of a support tube discussed herein may be approximately twelve inches long when measured between a first end of the support tube and a second end of the support tube. In yet another exemplary embodiment, another length of a support tube discussed herein may be between six inches up to about twelve inches when measured between a first end of the support tube and a second end of the support tube. In yet another exemplary embodiment, another length of a support tube discussed herein may be at least twelve inches when measured between a first end of the support tube and a second end of the support tube.

Figure 1:
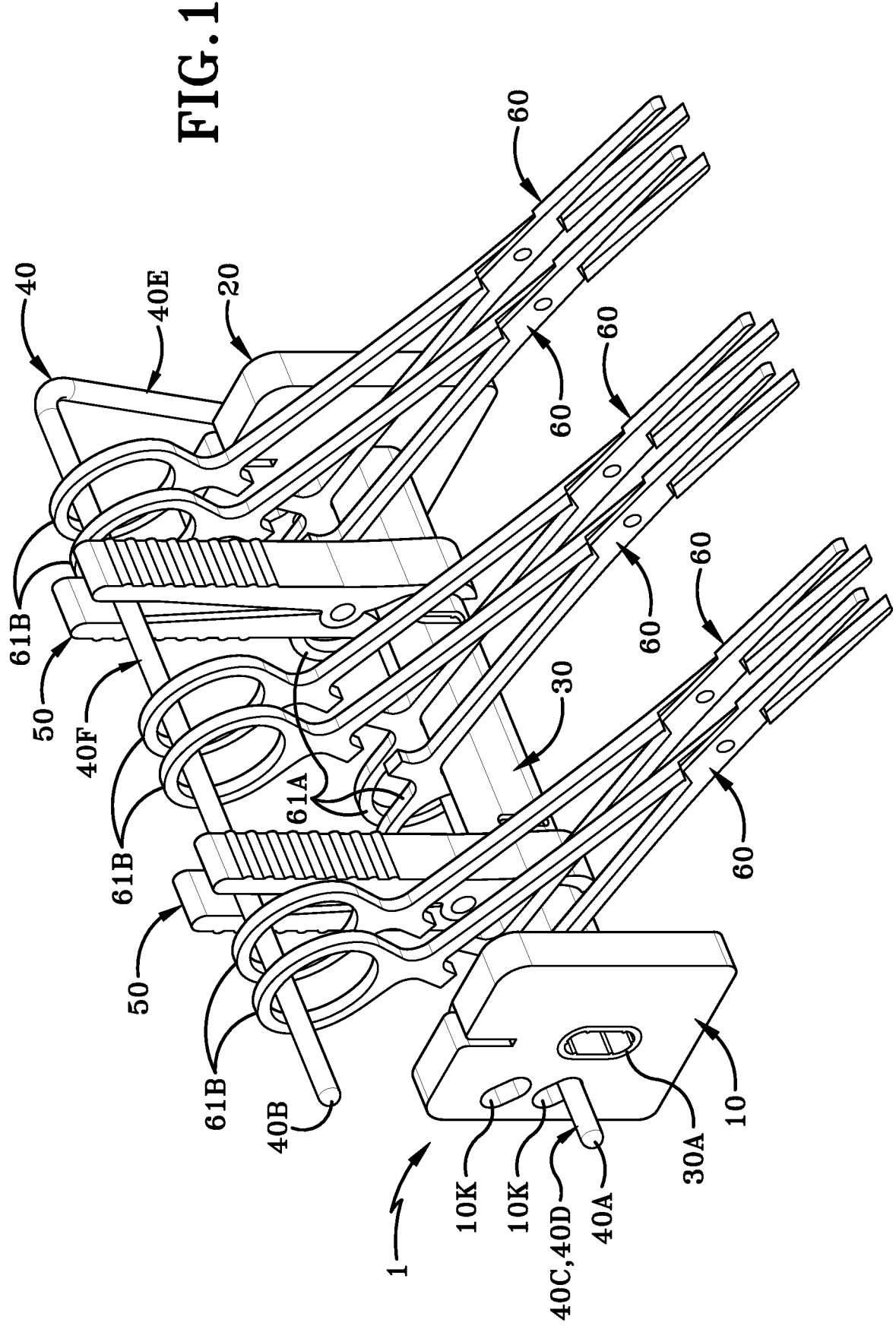
FIG. 1 (FIG. 1) is a front, top, first side isometric perspective view of a surgical instrument stand apparatus in accordance with one aspect of the present disclosure, wherein a set of first surgical instruments is supported by the surgical instrument stand apparatus with a first stand accessory and a set of clips.

Stand 1 may also be equipped with at least one first stand accessory or stringer bar 40. As best seen in FIG. 1, the stringer bar 40 includes a first end 40A, a second end 40B opposite to the first end 40A, and a cylindrical wall 40C that extends between the first end 40A and the second end 40B. The stringer bar 40 also includes a first portion 40D that extends from the first end 40A to a second portion 40E where the first portion 40D and the second portion 40E are orthogonal to one another. The stringer bar 40 also includes a third portion 40F that extends from the second end 40B to the second portion 40E where the second portion 40E and the third portion 40F are orthogonal to one another. In the present disclosure, the stringer bar 40 is provided in a U-shaped configuration in order to support and maintain handles and/or grips of surgical instruments on the stand 1. In one exemplary embodiment, any conventional or commercially available stringer or similar device may be equipped with stand 1 for supporting surgical instruments on the stand 1. Such use of the stringer bar 40 is discussed in greater detail below.

Stand 1 may also be equipped with one or more clips 50. As best seen in FIG. 1, clips 50 operably engage with the support tube 30 at any position between the first foot 10 and the second foot 20. In the present disclosure, two clips 50 are shown being clamped with the support tube 30 to separate and/or organize a set of first surgical instruments 60 into desired groups. In other exemplary embodiments, any suitable number of clips 50 may be clamped with the support tube 30 to separate and/or organize a set of first surgical instruments 60 into a desired number of groups. In one exemplary embodiment, clips 50 discussed and illustrated herein may be clips disclosed in U.S. patent application Ser. No. 12/315,839 with the title "SURGICAL STANDS, SURGICAL INSTRUMENT ORGANIZER ASSEMBLIES, AND METHODS OF USE THEREFOR." In other exemplary embodiments, clips 50 discussed and illustrated herein may also be conventional and/or commercially available surgical clips.

Having now discussed the components of the stand 1 and other accessories and/or equipment that may be equipped with the stand 1, methods of assembling stand 1 and methods of using stand 1 with surgical instruments are now discussed in greater detail below.

Prior to introducing a set of first surgical instruments 60 to the stand 1, a medical professional or user may assemble a single stand 1 (or more than one stand 1 if desired) for a surgical or medical procedure. Initially, the user may grab the first foot 10 and the support tube 30 to begin assembling the stand 1. Upon assembly, the user introduces the first end 30A of the support tube 30 into the central opening 10J of the first foot 10 to engage the first foot 10 and the support tube 30 with one another. The first projection 30J1 of the set of projections 30J may also provide attachment means inside of the central opening 10J of the first foot 10 to frictionally fit the first foot 10 and the support tube 30 with one another. Subsequently, the user introduces the second end 30B of the support tube 30 into the central opening 20J of the second foot 20 to engage the second foot 20 and the support tube 30 with one another. The second projection 30J2 of the set of projections 30J may also provide attachment means inside of the central opening 20J of the second foot 20 to frictionally fit the second foot 20 and the support tube 30 with one another.

Upon assembly of the stand 1, the user may then introduce the set of first surgical instruments 60 to the stand 1. Once introduced, each surgical instrument of the set of first surgical instruments 60 illustrated herein may rest on and be supported by the support tube 30. The user may then introduce one or more clips 50 to the stand 1 to organize and/or arrange the set of first surgical instruments 60 into one or more desired groups. As best seen in FIG. 1, two clips 50 are shown being clamped to the support tube 30 at two locations between the first end 30A and the second end 30B to divide and/or separate the set of first surgical instruments into three distinct groups. It should be understood that the user may introduce and clamp the clips 50 with the support tube 30 prior to introducing the set of first surgical instrument 60 to the stand 1.

Once the clips 50 and the set of first surgical instruments 60 are provided with stand 1, user may then introduce and temporarily engage a stringer bar 40 with the stand 1 and the set of first surgical instruments 60. As best seen in FIG. 1, the first end 40A of the stringer bar 40 may pass through a second accessory opening 20K2 of the pair of accessory openings 20K of the second foot 20. The first end 40A of the stringer bar 40 also passes through the second accessory opening 10K2 of the pair of accessory openings 10K of the first foot 10 given that the second accessory opening 10K2 of the pair of accessory openings 10K of the first foot 10 and the second accessory opening 20K2 of the pair of accessory openings 20K of the second foot 20 are coaxial with one another when stand 1 is assembled. The user continues to pass the first end 40A of the stringer bar 40 through the first foot 10 and the second foot 20 until the first portion 40D is supported and engaged with the first foot 10 and the second foot 20 inside of the second accessory opening 10K2 of the pair of accessory openings 10K of the first foot 10 and the second accessory opening 20K2 of the pair of accessory openings 20K of the second foot 20. As the first end 40A passes through the first foot 10 and the second foot 20, the first end 40A of the stringer bar 40 simultaneously passes through first handles and/or grips 61A of the set of first surgical instruments 60 so that the first portion 40D hangs and supports the set of first surgical instruments 60. As the first end 40A passes through the first foot 10 and the second foot 20, the second end 40B of the stringer bar 40 may simultaneously (or subsequently) pass through second handles and/or grips 61B of the set of first surgical instruments 60 opposite to the first handles and/or grips 61A of the set of first surgical instruments 60. Once the second end 40B passes through second handles and/or grips 61B of the set of first surgical instruments 60, the third portion 40F supports the set of first surgical instruments 60 to maintain the set of first surgical instruments 60 at an open position. Upon such engagement of the stand 1, the stringer bar 40, the clips 50, and the set of first surgical instruments 60, the user may then collectively transport the stand 1, the stringer bar 40, the clips 50, and the set of first surgical instruments 60 to desired locations.

Figure 6:
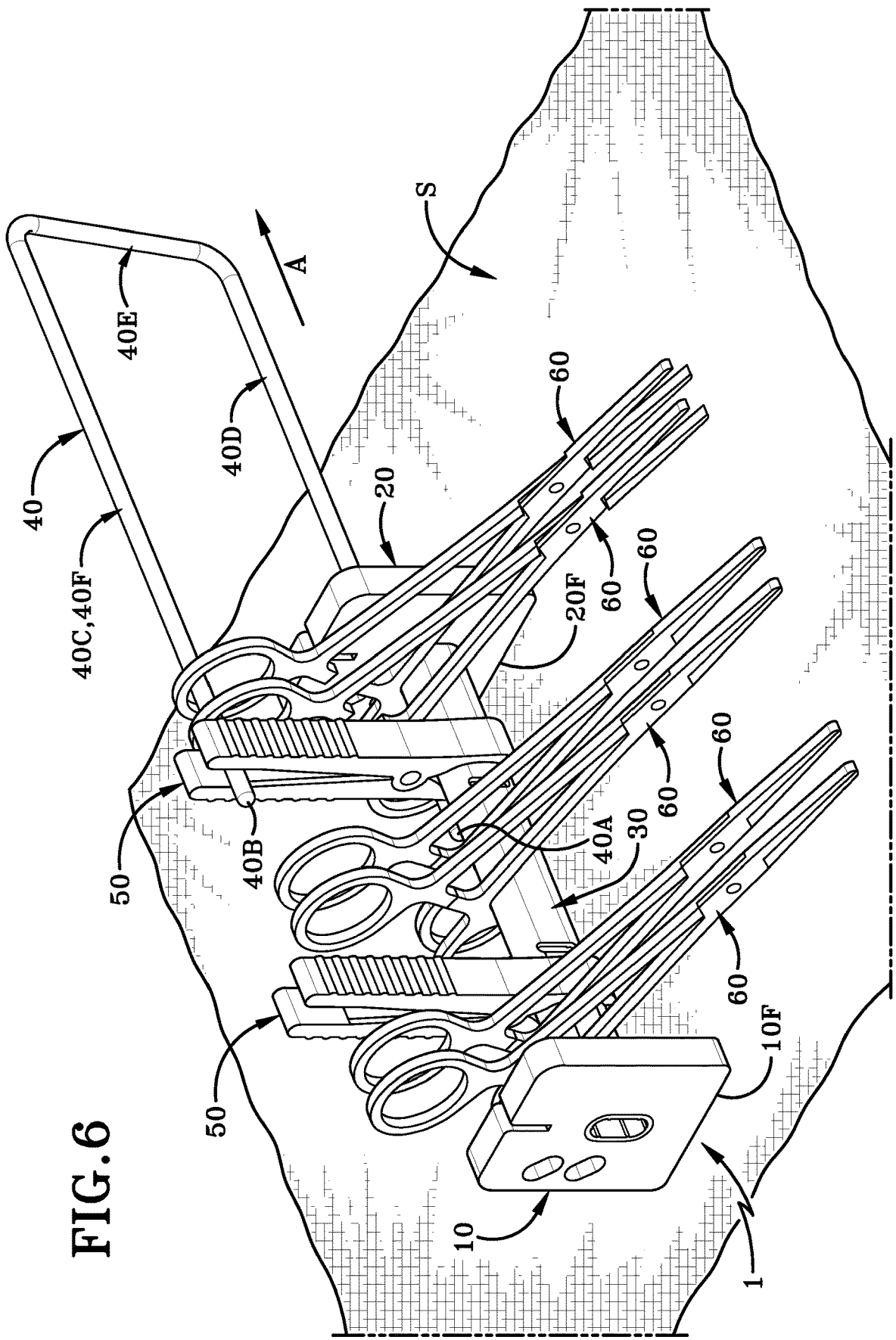
FIG. 6 (FIG. 6) is an operational view of the surgical instrument stand apparatus being placed on a surgical table while holding the set of first surgical instruments and the first stand accessory being removed from the surgical instrument stand apparatus FIG. 7 (FIG. 7) is another operational view of the surgical instrument stand apparatus being sterilized in a sterilization apparatus while holding the set of first surgical instruments with the first stand accessory and the set of clips.

In one instance, and as best seen in FIG. 6, the user may collectively transport the stand 1, the stringer bar 40, the clips 50, and the set of first surgical instruments 60 to a support surface or surgical tray/table (generally referred to as "S" in FIG. 6) for a surgical or medical procedure. Once the stand 1, the stringer bar 40, the clips 50, and the set of first surgical instruments 60 are resting on the support surface, the user may then remove the stringer bar 40 from the stand 1 and the set of first surgical instruments 60 so users or medical professions may simply retrieve and remove one or more surgical instruments of the set of first surgical instruments from the stand 1. Such removal of the stringer bar 40 is denoted by an arrow labeled "A" in FIG. 6. Once the stringer bar 40 is removed, the set of first surgical instruments 60 rests on and is supported by the support tube 30 and the clips 50 until users or medical professions retrieve and remove one or more surgical instruments of the set of first surgical instruments from the stand 1.

Figure 7:
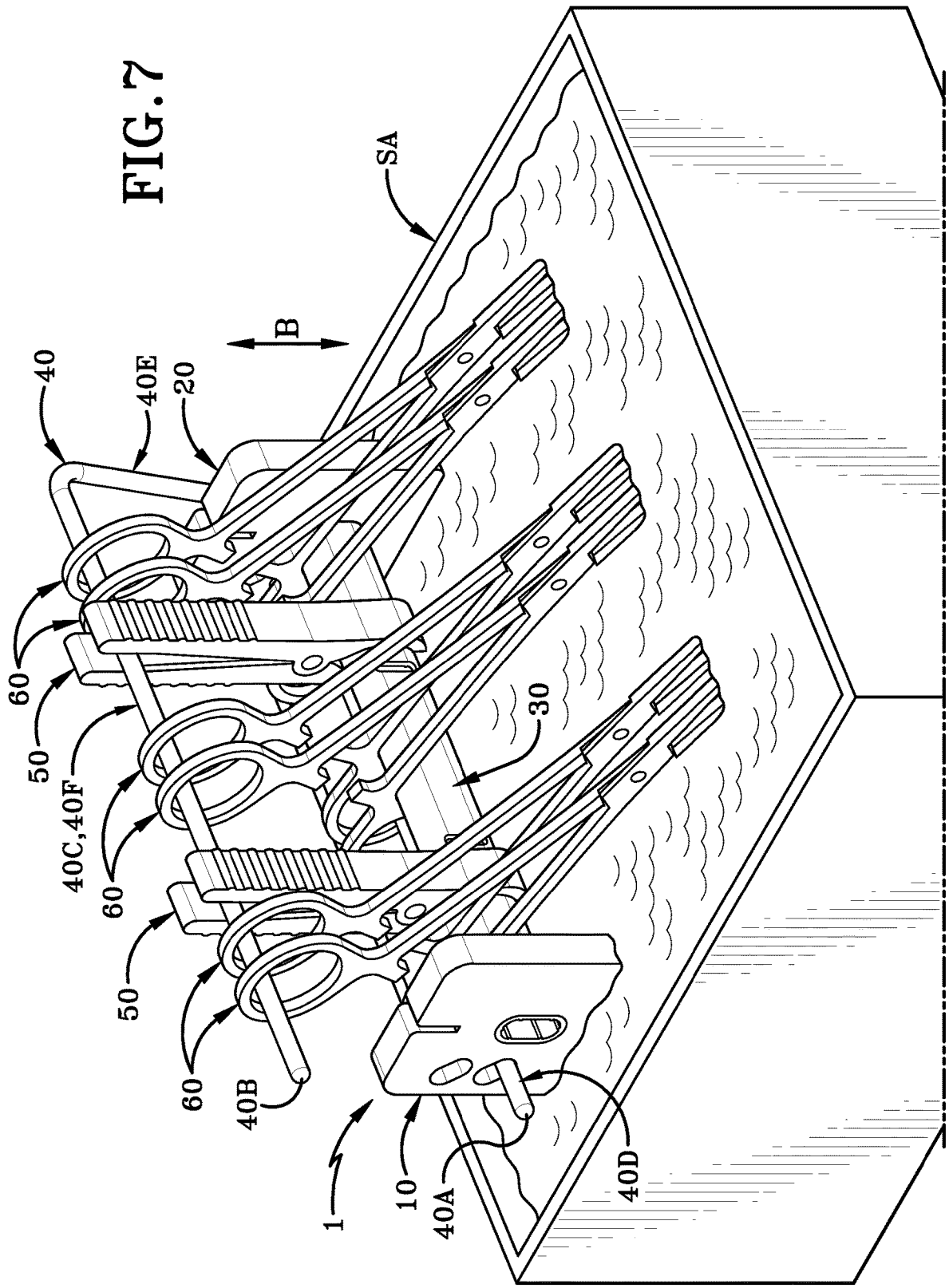

In another instance, and as best seen in FIG. 7, the user may collectively transport used and/or non-sanitary stand 1, the stringer bar 40, the clips 50, and the set of first surgical instruments 60 to a sterilization apparatus (generally referred to as "SA" in FIG. 7). In this instance, the used and/or non-sanitary stand 1, the stringer bar 40, the clips 50, and the set of first surgical instruments 60 are placed into the sterilization apparatus for sterilizing and/or cleaning purposes due to the devices and/or apparatuses being used in a previous surgical or medical procedure. It should be understood that a user may reengage the stringer bar 40 with the used stand 1 and the used set of first surgical instruments 60 to maintain the used set of first surgical instruments 60 with the stand 1 during sterilization and/or cleaning procedures. While not illustrated herein, the stand 1 may also be disassembled such that the first foot 10, the second foot 20, and the support tube 30 are placed into a sterilization apparatus that is illustrated herein or another commercially-available sterilizing apparatus for sterilizing and/or cleaning purposes after being used in a surgical or medical procedure.

Figure 10:
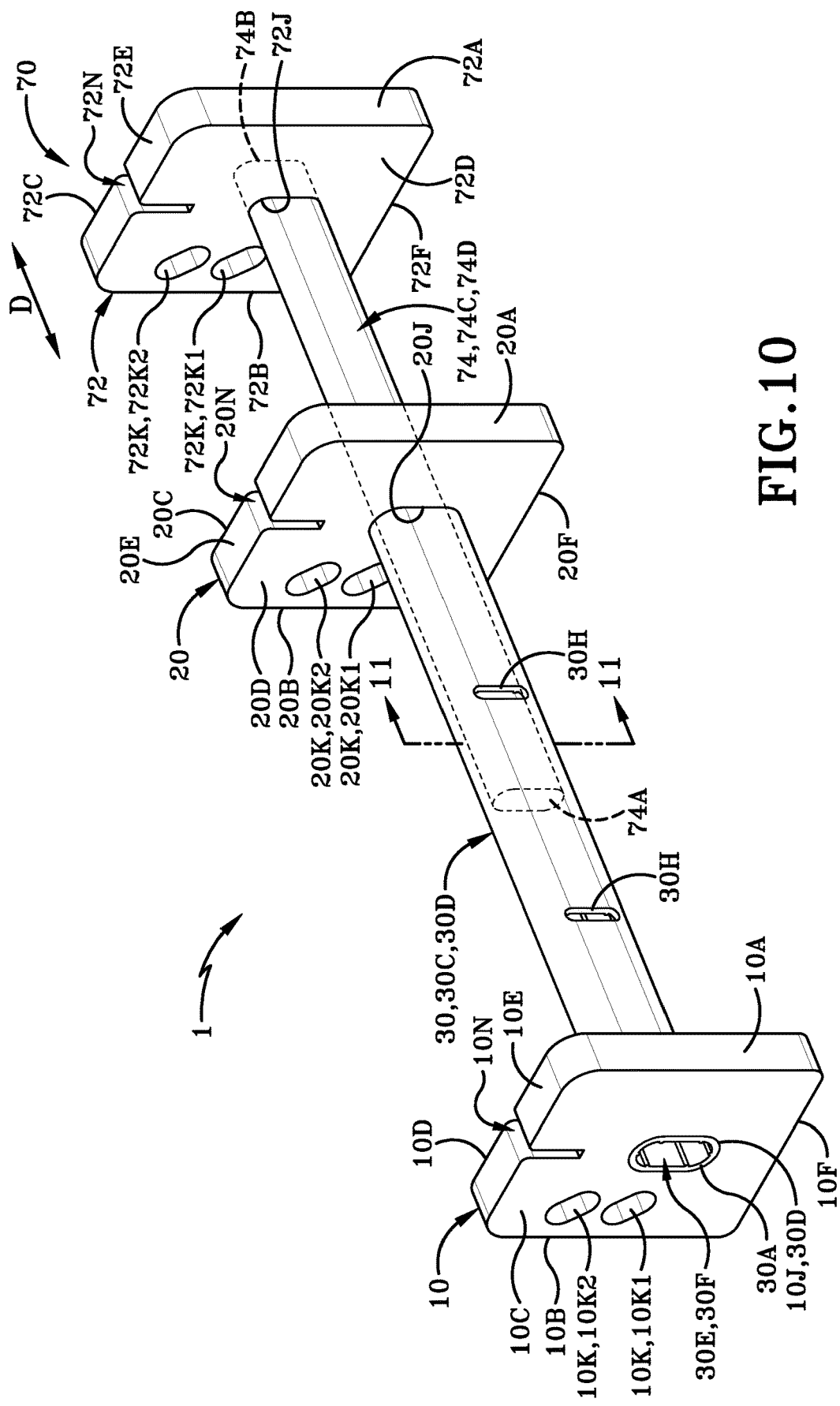
FIG. 10 (FIG. 10) is a front, top, first side isometric perspective view of the surgical instrument stand apparatus in accordance with another aspect of the present disclosure, wherein at least one expansion assembly is engaged with a support tube of the surgical instrument stand apparatus.

Stand 1 may also be equipped with an expansion assembly 70. As best seen in FIG. 10, the expansion assembly 70 is selectively operably engageable with the support tube 30 at the first end 30A of the support tube 30 or at the second end 30B of the support tube 30. It should be understood that the expansion assembly 70 is also slidably moveable with the support tube 30 to vary the overall length of the stand 1 (includes the first foot 10, the second foot 20, and the support tube 30) and the expansion assembly 70; such linear movement of the expansion assembly 70 is denoted by a double arrow labeled "B" in FIGS. 10 and 18. Such components that form the expansion assembly 70 are discussed in greater detail below.

Expansion assembly 70 includes an expansion foot 72. In the present disclosure, certain features of the expansion foot 72 are identical to certain features of the first foot 10. As such, a front end 72A, a rear end 72B, a first side 72C, a second side 72D, a top end 72E, a bottom end 72F, a pair of accessory openings 72K, and an expansion slit 72N of the expansion foot 72 are identical to the front end 10A, rear end 10B, outer side 10C, inner side 10D, top end 10E, bottom end 10F, pair of accessory openings 10K, and the first slit 10N of the first foot 10. It should be understood that, while not illustrated herein, the overall height 10G and the overall width 10H of the first foot 10 applies equally to an overall height and overall width of the expansion foot 72. It should also be understood that, while not illustrated herein, the pair of axes 10L and the angle 10M of the pair of accessory openings 10K of the first foot 10 applies equally to the pair of accessory openings 72K of the expansion foot 72. It should also be understood that, while not illustrated herein, the interior vertical walls 10N1 and the internal base wall 10N2 that define the first slit 10N having the slit height 10P and the slit width 10Q applies equally to the expansion slit 72N of the expansion foot 72.

However, the expansion foot 72 includes different features and/or configurations when compared to the first foot 10. As best seen in FIG. 12, the expansion foot 72 includes a central opening 72J that is similar to the central opening 10J of the first foot 10. In this embodiment, however, an inner diameter of the central opening 72J is less than and/or smaller than an inner diameter of the central opening 10J of the first foot 10 due to an outer diameter of an expansion support bar of the expansion assembly 70, which is discussed in greater detail below.

While expansion foot 72 defines the pair of accessory openings 72K, an expansion foot or any foot discussed and illustrated herein may define any suitable number of accessory openings as dictated by the implementation of the accessory openings, including the number of instrument stringers or first stand accessories that are intended to be received by an expansion foot or any foot of a stand mentioned herein. Examples of suitable numbers of accessory openings defined in an expansion foot or any foot discussed and illustrated herein include at least one, two, a plurality, three, four, five, and other suitable numbers of accessory openings that may be defined in a foot discussed and illustrated herein. In one exemplary embodiment, a first set of accessory openings may be defined at a front end of an expansion foot, and a second set of accessory openings may be defined at a rear end of the expansion foot opposite to the first set of accessory openings.

Expansion assembly 70 also includes an expansion support bar 74 that operably engages with the support tube 30 and the expansion foot 72. As best seen in FIG. 12, the expansion support bar 74 includes a first end 74A, a second end 74B that is longitudinally opposite to the first end 74A, a wall 74C that extends longitudinally between the first end 74A and the second end 74B, and a longitudinal direction defined therebetween. The expansion support bar 74 also includes an exterior surface 74D that extends along the entire length of the wall 74C between the first end 74A and the second end 74B. The expansion support bar 74 also defines an outer diameter 74E that is continuous along the wall 74C between the first end 74A and the second end 74B. In the present disclosure, the outer diameter 74E of the expansion support bar 74 is less than the inner diameter 30K of the support tube 30 so that the expansion support bar 74 is received by and engages with the support tube 30 inside of the passageway 30F; such assembly of the expansion assembly with the stand 1 is discussed in greater detail below.

Still referring to expansion support bar 74, expansion support bar 74 may also include a projection 74F. As best seen in FIG. 12, the projection 74F is positioned at the second end 74B of the expansion support bar 74 and extends outwardly from the exterior surface 74D. Such inclusion of the projections 74F may provide attachment means between the expansion foot 72 and the expansion support bar 74 when assembled with one another. Stated differently, expansion support bar 74 frictionally fits with the expansion foot 72 due to the projection 74F pressing against an interior wall defining the central opening 72J of the expansion foot 72.

Still referring to expansion support bar 74, the expansion support bar 74 may also include an end identifier 74G. As best seen in FIG. 12, the end identifier 74 extends longitudinally from the first end 74A towards a location that is defined between the first end 74A and the second end 74B. In one exemplary embodiment, the end identifier 74 may be shown as a series of arrows that extends longitudinally from the first end 74A towards a location that is defined between the first end 74A and the second end 74B. In operation, the end identifier 74G may indicate and/or signal to a user of the stand 1 and the expansion assembly 70 that the end of the expansions support bar 74 is near when moving the expansion assembly 70 away from the stand 1. Such warning and/or indication prevents the user from accidently or incidentally removing the expansion support bar 74 from the support tube 30 when adjusting the expansion assembly 70. It should be understood that additional measurement markings and/or indicia may be used to determine how close the first end 74A is based on specific markings defining the end identifier 74G.

It should be understood that the expansion support tube may define any suitable length necessary for transporting and organizing surgical and/or medical equipment. In one exemplary embodiment, a length of an expansion support tube discussed herein may be approximately six inches long when measured between a first end of the support tube and a second end of the support tube. In another exemplary embodiment, another length of an expansion support tube discussed herein may be approximately twelve inches long when measured between a first end of the support tube and a second end of the support tube. In yet another exemplary embodiment, another length of an expansion support tube discussed herein may be between six inches up to about twelve inches when measured between a first end of the support tube and a second end of the support tube. In yet another exemplary embodiment, another length of an expansion support tube discussed herein may be at least twelve inches when measured between a first end of the support tube and a second end of the support tube.

Having now described the components of the expansion assembly 70, a method of assembling the expansion assembly 70 with the stand 1 is discussed in greater detail below.

Initially, the user may retrieve the expansion foot 72 and the expansion support bar 74 to begin assembling the expansion assembly 70. Upon assembly, the user introduces the second end 74B of the expansion support bar 74 into the central opening 72J of the expansion foot 72 to engage the expansion foot 72 and the expansion support bar 74 with one another. The projection 74J of the expansion support bar 74 may also provide attachment means inside of the central opening 72J of the expansion foot 72 to frictionally fit the expansion foot 72 and the expansion support bar 74 with one another.

Once the expansion assembly 70 is built, the user may then assembly the expansion assembly 70 with the assembled stand 1 by inserting the first end 74A of the expansion support bar 74 into the passageway 30F of the support tube 30 at the first end 30A or the second end 30B. In one example, and as best seen in FIGS. 10-11, the user inserts the first end 74A of the expansion support bar 74 through the second end 30B of the support tube 30 and into the passageway 30F of the support tube 30. Upon insertion of the expansion support bar 74, the set of internal ridges 30G grips and engages with the exterior surface 74D of the expansion support bar 74 to frictionally fit the expansion support bar 74 with the support tube 30 (see FIG. 11). The user may continue to insert the expansion support bar 74 into the support tube 30 until a desired distance is met between the second foot 20 and the expansion foot 72. The user may use and view through one of the apertures of the set of apertures 30H defined in the support tube 30 to determine the position of the first end 74A of the expansion support bar 74 (or at least a portion of the expansion support bar 74) inside of the support tube 30.

Once the stand 1 and expansion assembly 70 are assembled with one another, user may introduce and equip one or more stringer bars 40 with the stand 1 and/or the expansion assembly 70 and one or more clips 50 with the stand 1 and/or the expansion assembly 70 to support and/or hold two sets of first surgical instruments 60.

Figure 8:
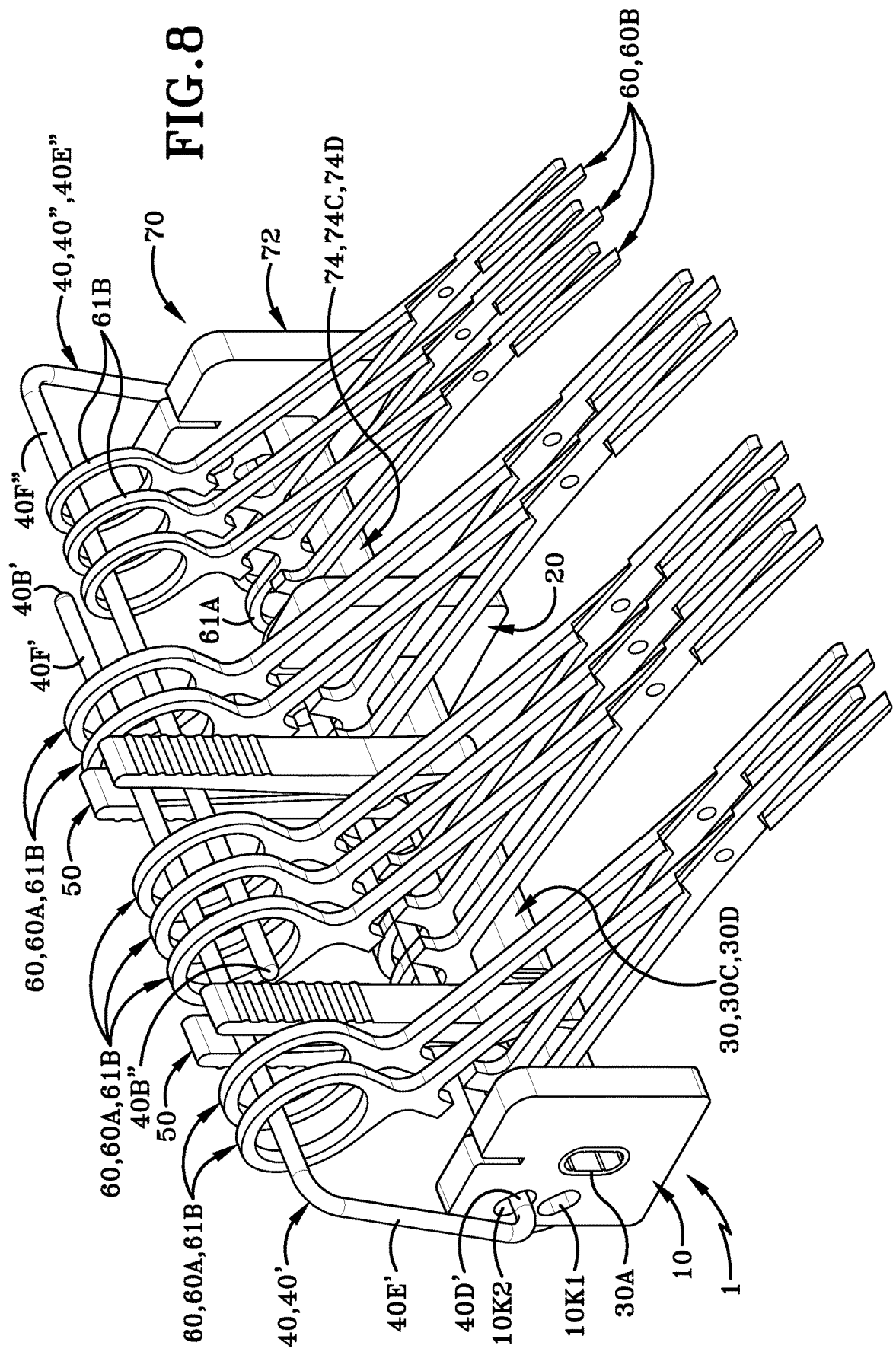
FIG. 8 (FIG. 8) is a front, top, first side isometric perspective view of the surgical instrument stand apparatus in accordance with another aspect of the present disclosure, wherein a first group of a set of first surgical instruments and a second group of a set of first surgical instruments are supported by the surgical instrument stand apparatus with first stand accessories and a set of clips.
Figure 9:
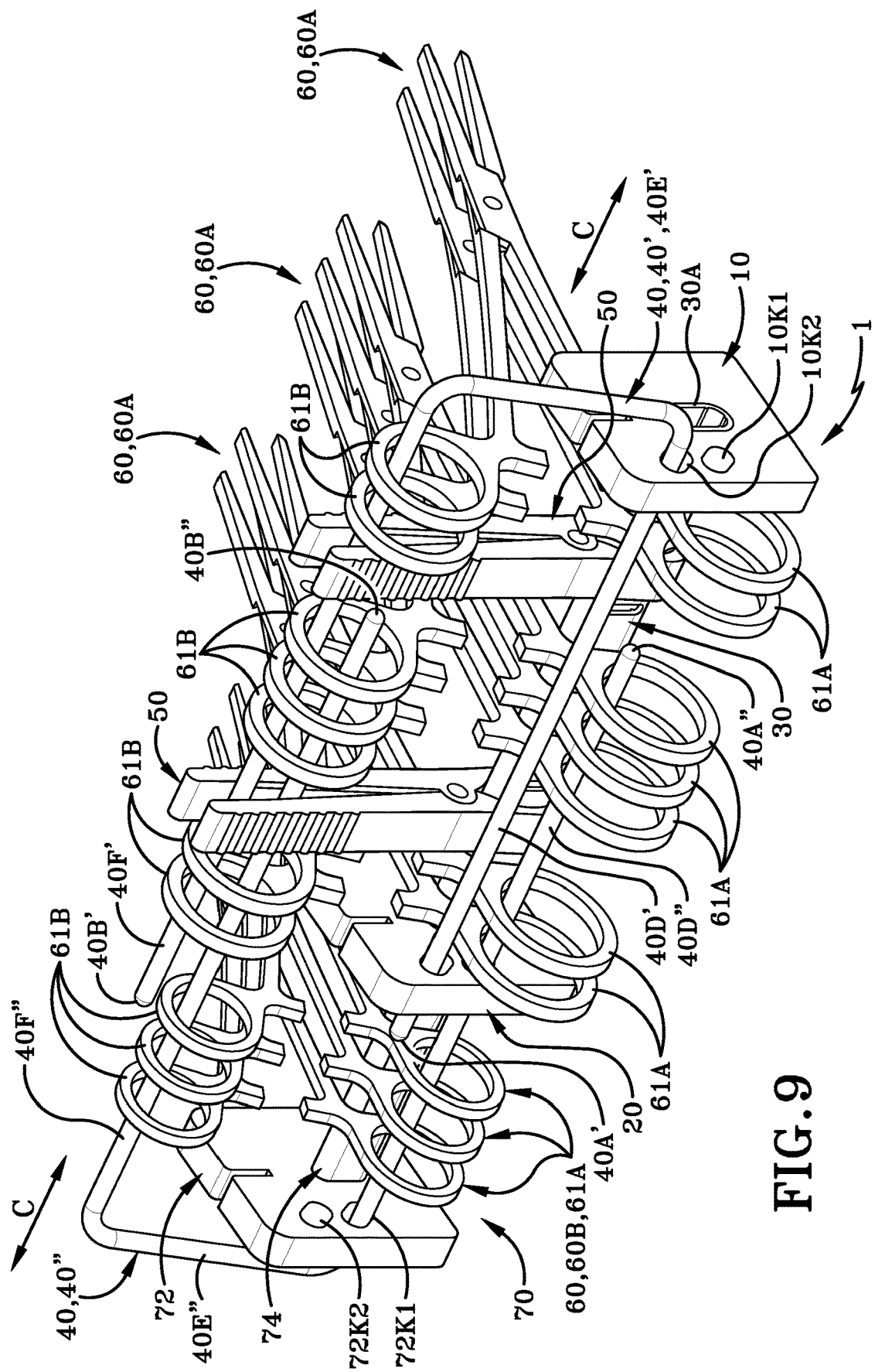
FIG. 9 (FIG. 9) is a rear, top, first side isometric perspective view of the surgical instrument stand apparatus shown in FIG. 8, wherein the first stand accessories are removable from the set of first surgical instruments.

In one embodiment, and as best seen in FIGS. 8-9, the user may introduce the two sets of first surgical instruments 60 to the stand 1. Once introduced, each surgical instrument of a first set of first surgical instruments 60A illustrated herein may rest on and be supported by the support tube 30, and each surgical instrument of a second set of first surgical instruments 60B illustrated herein may rest on and be supported by the expansion support bar 74. The user may then introduce one or more clips 50 to the stand 1 and to the expansion assembly 70 to organize and/or arrange the sets of first surgical instruments 60A, 60B in one or more desired groups. As best seen in FIGS. 8-9, two clips 50 are shown being clamped to the support tube 30 at two locations between the first end 30A and the second end 30B to divide and/or separate the first set of first surgical instruments 60A into three distinct groups while the second foot 20 separates the second set of first surgical instruments 60B from the first set of first surgical instruments 60A. It should be understood that the user may introduce and clamp the clips 50 with the support tube 30 or the expansion support bar 74 prior to introducing the sets of first surgical instrument 60A, 60B to the stand 1.

Once the clips 50 and the sets of first surgical instruments 60A, 60B are provided with stand 1, user may then introduce and temporarily engage two stringer bars 40', 40" with the stand 1, the expansion assembly 70, and the sets of first surgical instruments 60A, 60B. As best seen in FIGS. 8-9, the first end 40A' of the first stringer bar 40' may pass through the second accessory opening 20K2 of the pair of accessory openings 20K of the second foot 20. The first end 40A' of the first stringer bar 40' also passes through the second accessory opening 10K2 of the pair of accessory openings 10K of the first foot 10 given the second accessory opening 10K2 of the pair of accessory openings 10K of the first foot 10 and the second accessory opening 20K2 of the pair of accessory openings 20K of the second foot 20 are coaxial with one another when stand 1 is assembled. The user continues to pass the first end 40A' of the first stringer bar 40' through the first foot 10 and the second foot 20 until the first portion 40D' is supported and engaged with the first foot 10 and the second foot 20. As the first end 40A' passes through the first foot 10 and the second foot 20, the second end 40B' of the stringer bar 40' simultaneously passes through second handles and/or grips 61B of the first set of first surgical instruments 60A so that the third portion 40F' hangs and supports the first set of first surgical instruments 60A.

Similarly, and as best seen in FIGS. 8-9, the first end 40A" of the second stringer bar 40" may pass through a first accessory opening 72K1 of the pair of accessory openings 72K of the expansion foot 72. The first end 40A" of the second stringer bar 40" also passes through the first accessory opening 20K1 of the pair of accessory openings 20K of the second foot 20 given the first accessory opening 20K1 of the pair of accessory openings 20K of the second foot 20 and the first accessory opening 72K1 of the pair of accessory openings 72K of the expansion foot 72 are coaxial with one another when stand 1 and expansion assembly 70 are assembled. The user continues to pass the first end 40A" of the second stringer bar 40" through the second foot 20 until the first portion 40D" of the second stringer bar 40" is supported and engaged with the second foot 20 and the expansion foot 72. As the first end 40A" passes through the second foot 20 and the expansion foot 72, the first end 40A" of the second stringer bar 40" simultaneously passes through first handles and/or grips 61A of the second set of first surgical instruments 60B and first handles and/or grips 61A of the first set of first surgical instruments 60A so that the first portion 40D" supports some of the first set of first surgical instruments 60A and the second set of first surgical instruments 60B. As the first end 40A" passes through the second foot 20 and the expansion foot 72, the second end 40B" of the second stringer bar 40" simultaneously passes through second handles and/or grips 61B of the second set of first surgical instruments 60B and second handles and/or grips 61B of the first set of first surgical instruments 60A so that the third portion 40F" hangs and supports some of the first set of first surgical instruments 60A and the second set of first surgical instruments 60B. Upon such engagement of the stand 1, the stringer bars 40', 40", the clips 50, the sets of first surgical instruments 60, and the expansion assembly 70, the user may then collectively transport the stand 1, the stringer bar 40, the clips 50, the set of first surgical instruments 60, and the expansion assembly 70 to desired locations discussed herein and other suitable locations found in hospitals or other medical buildings and offices.

It should be understood that while two stringer bars 40 were used with the stand 1 and the expansion assembly 70, any number of stringer bars may be equipped with just the stand 1, a combination of the stand 1 and the expansion assembly 70, a combination of the stand and at least two expansion assemblies 70, and other combinations or configurations of the stand 1 discussed herein.

Figure 13:
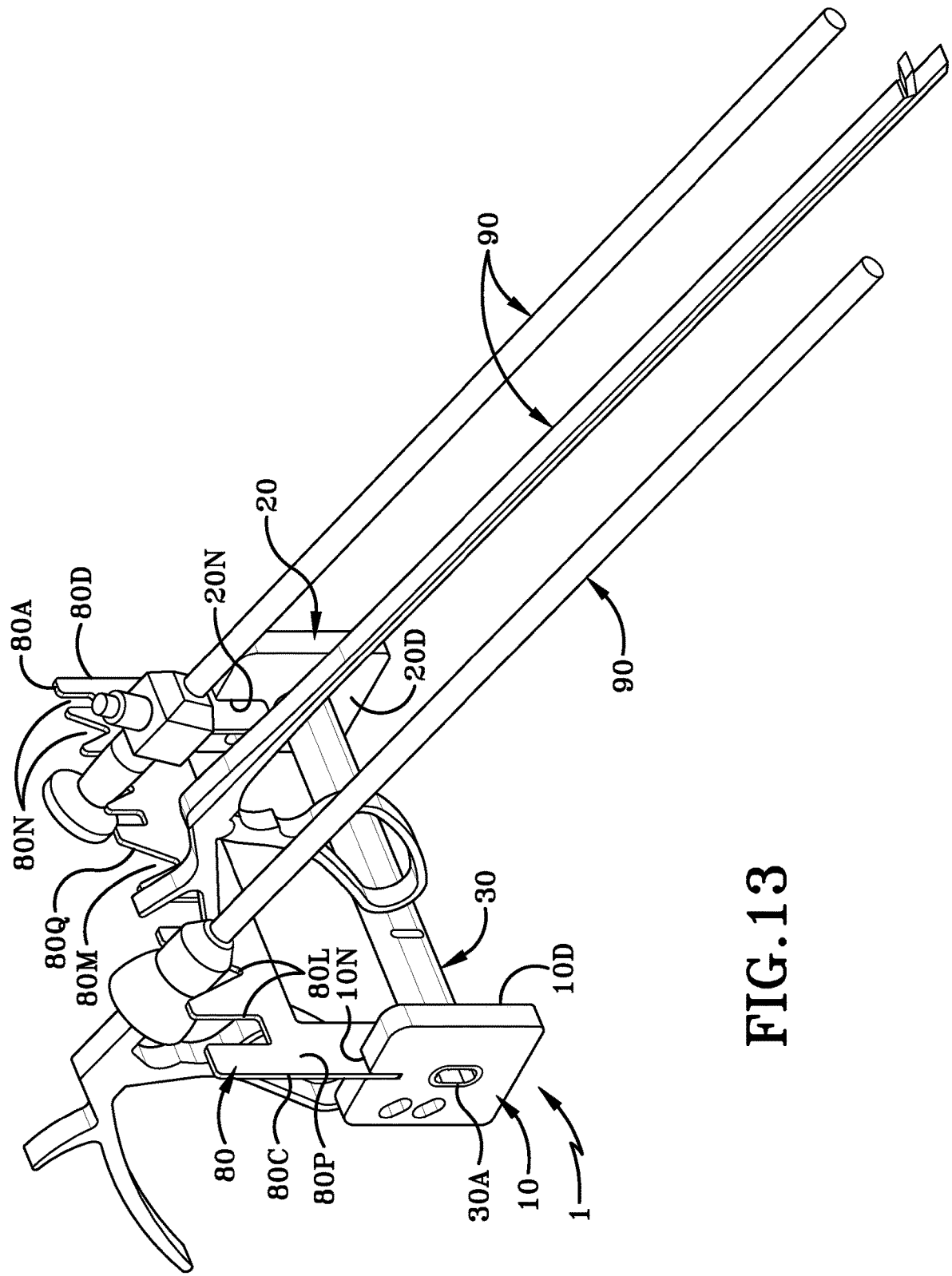
FIG. 13 (FIG. 13) is a front, top, first side isometric perspective view of the surgical instrument stand apparatus in accordance with another aspect of the present disclosure, wherein a set of second surgical instruments is supported by a second stand accessory that is equipped to the surgical instrument stand apparatus.

FIGS. 13-16 illustrate a rack or second stand accessory, generally referred to as 80, that operably engages with the stand 1 and/or expansion assembly 70 (if equipped). As best seen in FIG. 13, the rack 80 is configured to engage with at least the first foot 10 and the second foot 20 and to support one or more types of surgical equipment or instruments at an elevated position that is above the support tube 30. Such features and components of the rack 80 are discussed in greater detail below.

Figure 16:
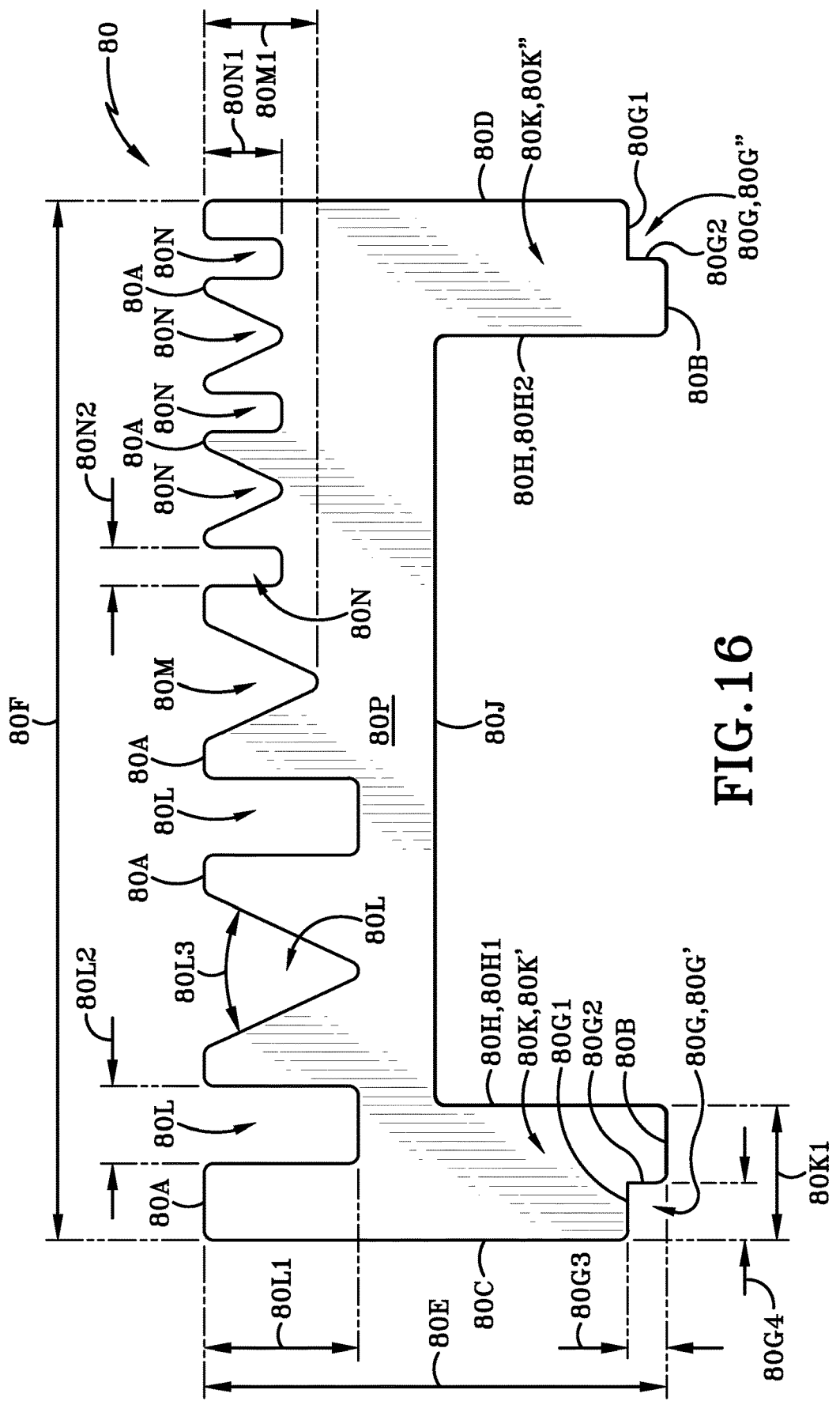
FIG. 16 (FIG. 16) is a front elevation view of the second stand accessory.

As best seen in FIG. 16, the rack 80 includes a top edge 80A, a bottom edge 80B that is vertically opposite to the top edge 80A, and a vertical direction defined therebetween. Rack 80 also includes a first side edge 80C that extends between the top edge 80A and the bottom edge 80B, and a second side edge 80D that extends between the top edge 80A and the bottom edge 80B and is opposite to the first side edge 80C. Rack 80 also defines an overall height 80E that is measured between the top edge 80A and the bottom edge 80B, and an overall length 80F that is measured between the first side edge 80C and the second side edge 80D. In the present disclosure, the overall length 80F of the rack 80 is greater than the overall height 80E and is equal to the overall length of the stand 1 measured between the outer sides 10C, 20C of the first foot 10 and the second foot 20. In other exemplary embodiments, any rack discussed herein may have any suitable height or length as dictated by the implantation of said rack.

Rack 80 also defines a pair of notches 80G wherein a first notch 80G' is defined at the bottom edge 80B near the first side edge 80C, and a second notch 80G" is defined at the bottom edge 80B near the second side edge 80D. Each notch of the pair of notches 80G is defined by a lower horizontal edge 80G1 that extends inwardly from the respective side edge 80C, 80D to a lower vertical edge 80G2. Each notch of the pair of notches 80G also defines a height 80G3 that is measured from the bottom edge 80B to the respective lower horizontal edge 80G1. Each notch of the pair of notches 80G also defines a width 80G4 that is measured from the lower vertical edge 80G2 to the respective side edge 80C, 80D. Rack 80 also includes a pair of interior vertical edges 80H where a first interior vertical edge 80H1 of the pair of interior vertical edges 80H extends vertically upward from the bottom edge 80B to an interior horizontal edge 80J of the rack 80. Similarly, a second interior vertical edge 80H2 of the pair of interior vertical edges 80H extends vertically upward from the bottom edge 80B to the interior horizontal edge 80J of the rack 80. In the present disclosure, the interior vertical edges 80H and the interior horizontal edge 80J collectively define a continuous U-shaped edge. Such U-shaped edge may become advantageous if a user would like to rest surgical instruments or devices on the support tube 30 without interference or hindrance created by the rack 80.

Still referring to rack 80, rack 80 also includes a pair of legs 80K. As best seen in FIG. 16, a first leg 80K' of the pair of legs 80K is defined between the first side edge 80C and the first interior vertical edge 80H1 and has a leg width 80K1, and a second leg 80K" of the pair of legs 80K is defined between the second side edge 80D and the second interior vertical edge 80H2 and has the leg width 80K1. In the present disclosure, the leg width 80K1 is greater than the width 80G4 of each notch of the pair of notches 80G and the slit widths (e.g., 10Q) defined by the first foot 10 and the second foot 20.

Still referring to rack 80, rack 80 defines at least one group or set of recesses along the top edge 80A of the rack 80. As best seen in FIG. 16, rack 80 defines a first group of recesses 80L that extends downwardly into the rack 80 from the top edge 80A towards the bottom edge 80B. In one instance, a recess of the first group of recesses 80L may be defined by a first notch height 80L1 and a first notch width 80L2 for receiving surgical instruments and/or devices that define a rectangular outer profile. In another instance, another recess of the first group of recesses 80L may be defined by a first notch angle 80L3 for receiving surgical instruments and/or devices that define a circular outer profile and/or tapered outer profile. In the present disclosure, angle 80L3 is an acute angle for receiving surgical instruments and/or devices that define a circular outer profile and/or tapered outer profile. In other exemplary embodiments, angle 80L3 may be any suitable angle for receiving surgical instruments and/or devices that define a circular outer profile and/or tapered outer profile.

Still referring to FIG. 16, rack 80 may also define a second group of recesses 80M that extends downwardly into the rack 80 from the top edge 80A towards the bottom edge 80B. In one instance, a recess of the second group of recesses 80M may define a second notch height 80M1 that is less than the first notch height 80L1 of the first group of recesses 80L. In this instance, notches of the second group of recesses 80M may receive surgical instruments and/or devices that define smaller outer profiles as compared to the outer profiles of the surgical instruments and/or devices received by the first group of recesses 80L.

Still referring to FIG. 16, rack 80 may also define a third group of recesses 80N that extends downwardly into the rack 80 from the top edge 80A towards the bottom edge 80B. In one instance, a recess of the third group of recesses 80N may be defined by a third notch height 80N1 and a second notch width 80N3 for receiving surgical instruments and/or devices that define a rectangular outer profile. In this instance, recesses of the third group of recesses 80N may receive surgical instruments and/or devices that define smaller outer profiles as compared to the outer profiles of the surgical instruments and/or devices received by the first group of recesses 80L and the second group of recesses 80M.

With such differences in size, shape, and configuration of the first group of recesses 80L, the second group of recesses 80M, and the third group of recesses 80N, the rack 80 provides users and medical professionals to rest and/or hang various types of surgical instruments and devices from the rack 80 when such surgical instruments and devices are not being used during surgical and/or medical procedures. The rack 80 also places the surgical instruments and devices at an elevated state so that users and medical professionals may quickly grasp and remove a desired surgical instrument or device or quickly place and rest the used surgical instrument or device at the desired position on the rack 80. The rack 80 also organizes various types of surgical instruments or devices based on the outer profiles or sizes of these surgical instruments or devices by placing and resting said surgical instruments into conforming recesses 80L, 80M, 80N defined in rack 80.

Figure 19:
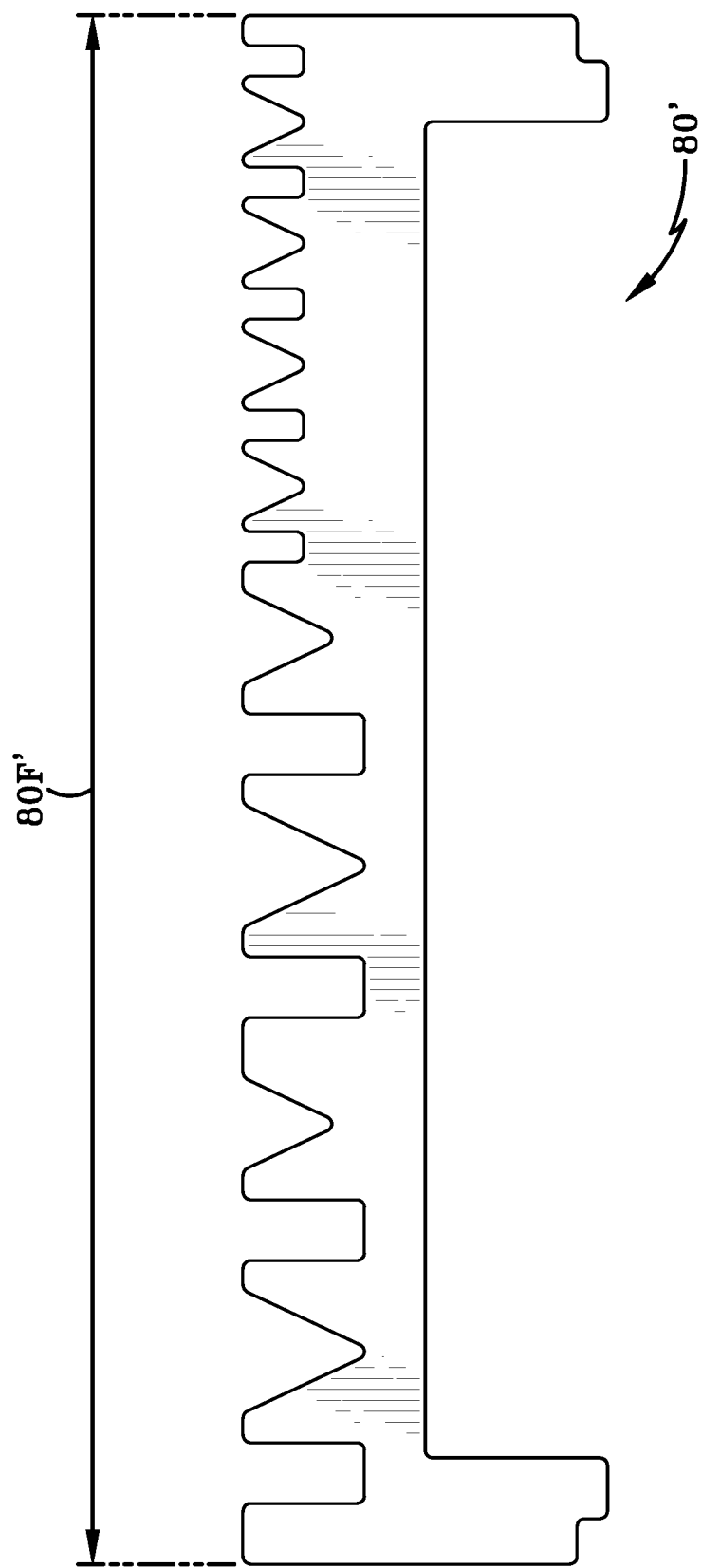
FIG. 19 (FIG. 19) is a front elevation view of an alternative second stand accessory.

While rack 80 defines a first group of recesses 80L, a second group of recesses 80M, and a third group of recesses 80N, a rack discussed and illustrated herein may include any suitable number of notches for resting and/or hanging various types of surgical instruments or devices for a particular surgical or medical procedure. In one example, and as best seen in FIG. 19, an alternative rack or second stand accessory 80' may define a greater number recesses or slots so a user may rest and/or hang a greater number of surgical instruments or devices as compared to the rack 80 discussed above. In this example, alternative rack 80' defines an overall length 80F' that is greater than the overall length 80F of the rack 80 discussed above. It should be noted that a user may desire to use alternative rack 80' when stand 1 is equipped with the expansion assembly 70 since alternative rack 80' is intended to engage with one of the first foot 10 and the second foot 20 of the stand 1 and the expansion foot 72 of the expansion assembly 70.

Figure 15:
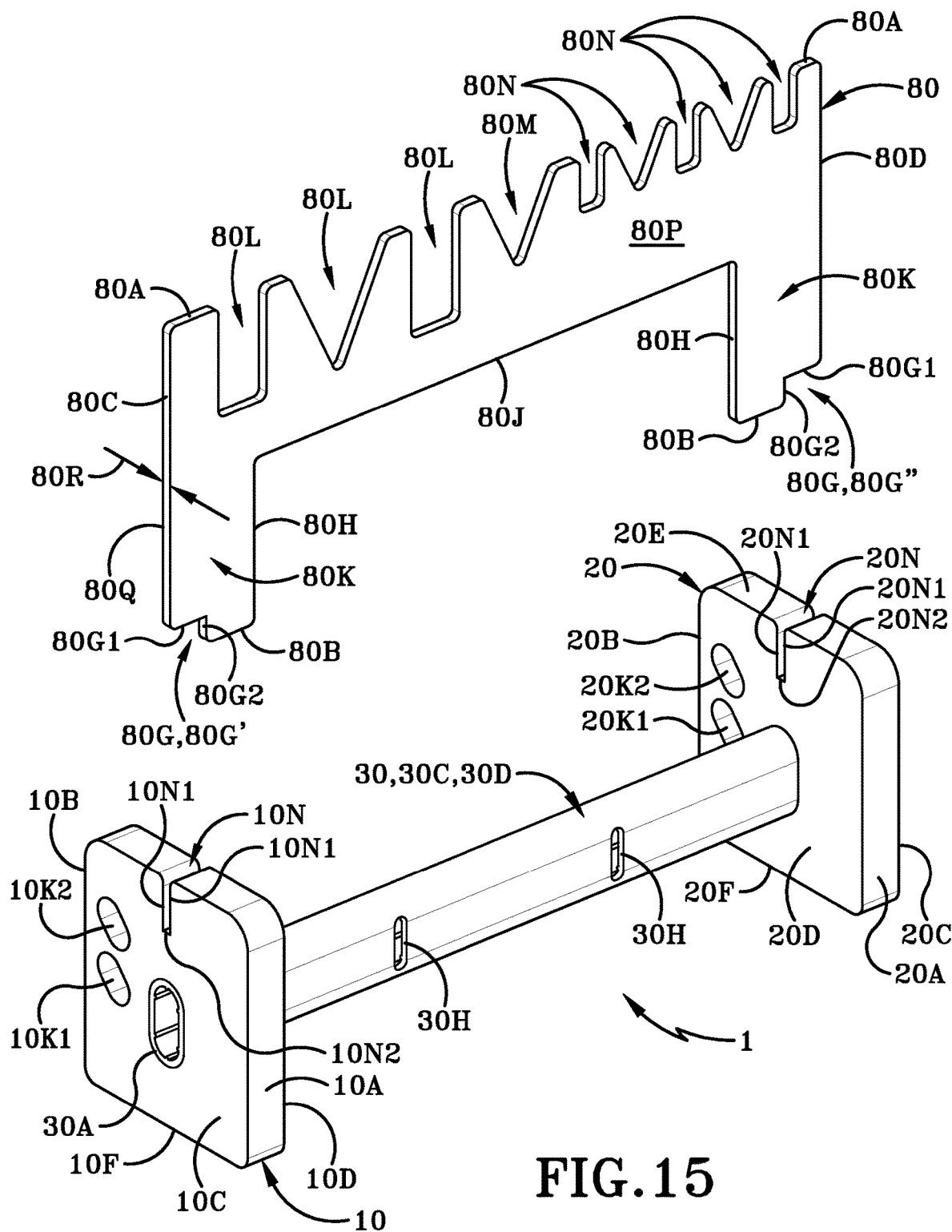
FIG. 15 (FIG. 15) is an exploded view of the surgical instrument stand apparatus and the second stand accessory.

Still referring to rack 80, rack 80 also defines a front surface 80P and a rear surface 80Q. As best seen in FIG. 15, the front surface 80P extends between the first side edge 80C and the second side edge 80D and is positioned ahead of the top edge 80A, the bottom edge 80B, the first side edge 80C, and the second side edge 80D. Still referring to FIG. 15, the rear surface 80Q also extends between the first side edge 80C and the second side edge 80D and is positioned behind the top edge 80A, the bottom edge 80B, the first side edge 80C, and the second side edge 80D. Rack 80 also defines an overall thickness 80R that is continuous along the entire length of the rack 80 from the first side edge 80C and the second side edge 80D. In the present disclosure, the overall thickness 80R of the rack 80 is less than the slit width 10Q of the first foot 10 (as well as the second foot 20) wherein the rack 80 frictionally fits inside of the first foot 10 and the second foot 20.

It should be understood that the rack 80 may define any suitable length necessary for transporting and organizing surgical and/or medical equipment. In one exemplary embodiment, a length of a rack discussed herein may be approximately six inches long when measured between a first side edge of the rack and a second side edge of the rack. In another exemplary embodiment, another length of a rack discussed herein may be approximately twelve inches long when measured between a first side edge of the rack and a second side edge of the rack. In yet another exemplary embodiment, another length of a rack discussed herein may be between six inches up to about twelve inches when measured between a first side edge of the rack and a second side edge of the rack. In yet another exemplary embodiment, another length of a rack discussed herein may be at least twelve inches when measured between a first side edge of the rack and a second side edge of the rack.

Having now described the features of rack 80, methods of assembling rack 80 with the stand 1 to rest and/or hang various types of surgical equipment from the rack 80 are discussed in greater detail below.

Figure 14:
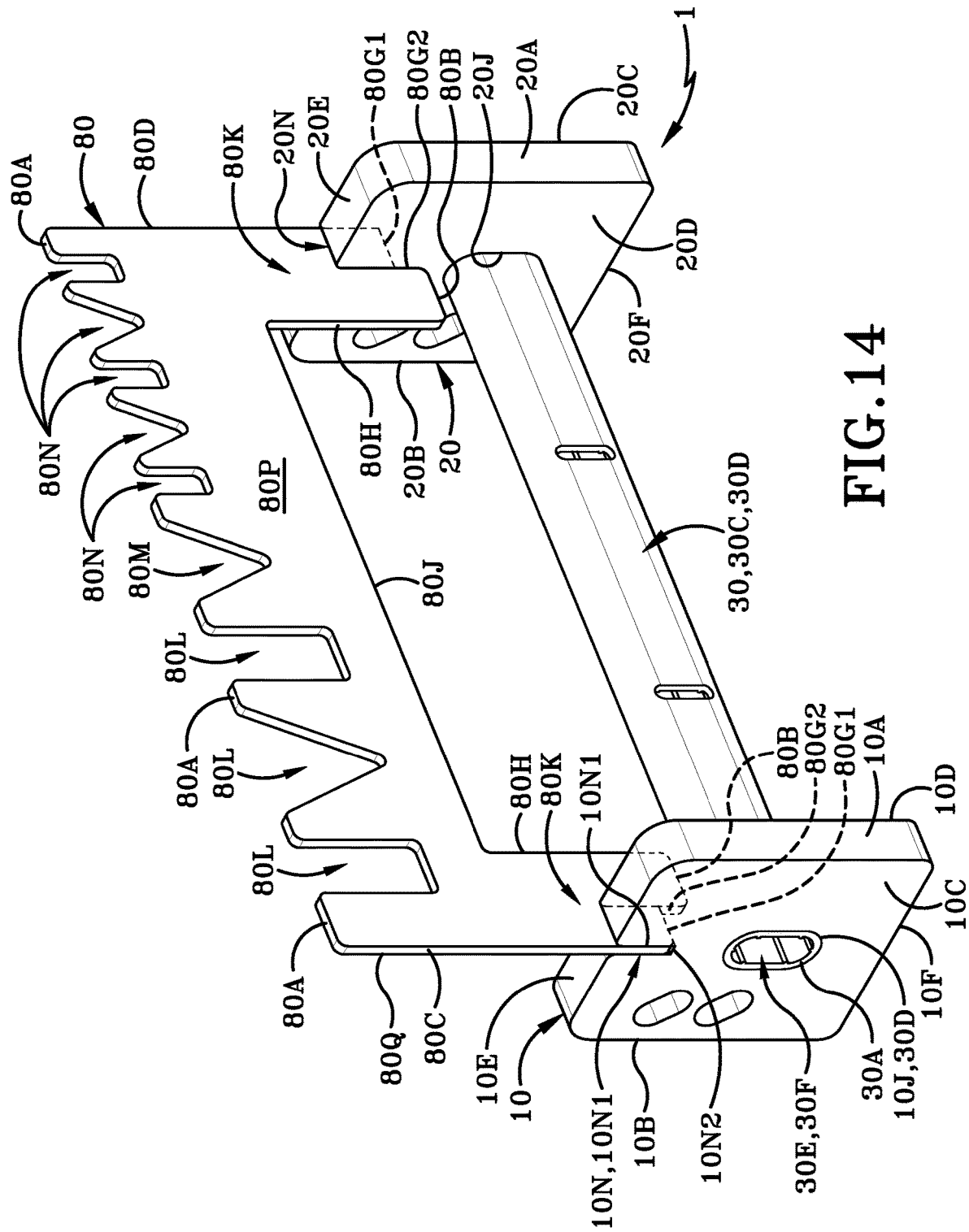
FIG. 14 (FIG. 14) is a front, top, first side isometric perspective view of the surgical instrument stand apparatus equipped with the second stand accessory as shown in FIG. 13.

Once the stand 1 is assembled, the user may then introduce and engage the rack 80 with the stand 1. As best seen in FIG. 14, the pair of notches 80G of the rack 80 is received by the first slit 10N of the first foot 10 and the second slit 20N of the second foot 20. The first slit 10N of the first foot 10 and the second slit 20N of the second foot 20 also receive portions of the rack 80 that are measured from the pair of notches 80G to a medial location between the top edge 80A and the pair of notches 80G. Such portions of the rack 80 that engage with first foot 10 and the second foot 20 inside of the first slit 10N and the second slit 20N include front surface 80P of the rack 80 and the rear surface 80Q of the rack 80. The lower vertical edges 80G2 that define the pair of notches 80G may also engage with the inner sides 10D, 20D of the first foot 10 and the second foot 20. Once the rack 80 is frictionally fit with the stand 1, users may then rest and hang a set of second surgical instruments 90 inside of one or more of the first group of recesses 80L, the second group of recesses 80M, and the third group of recesses 80N (see FIG. 13).

Figure 18:
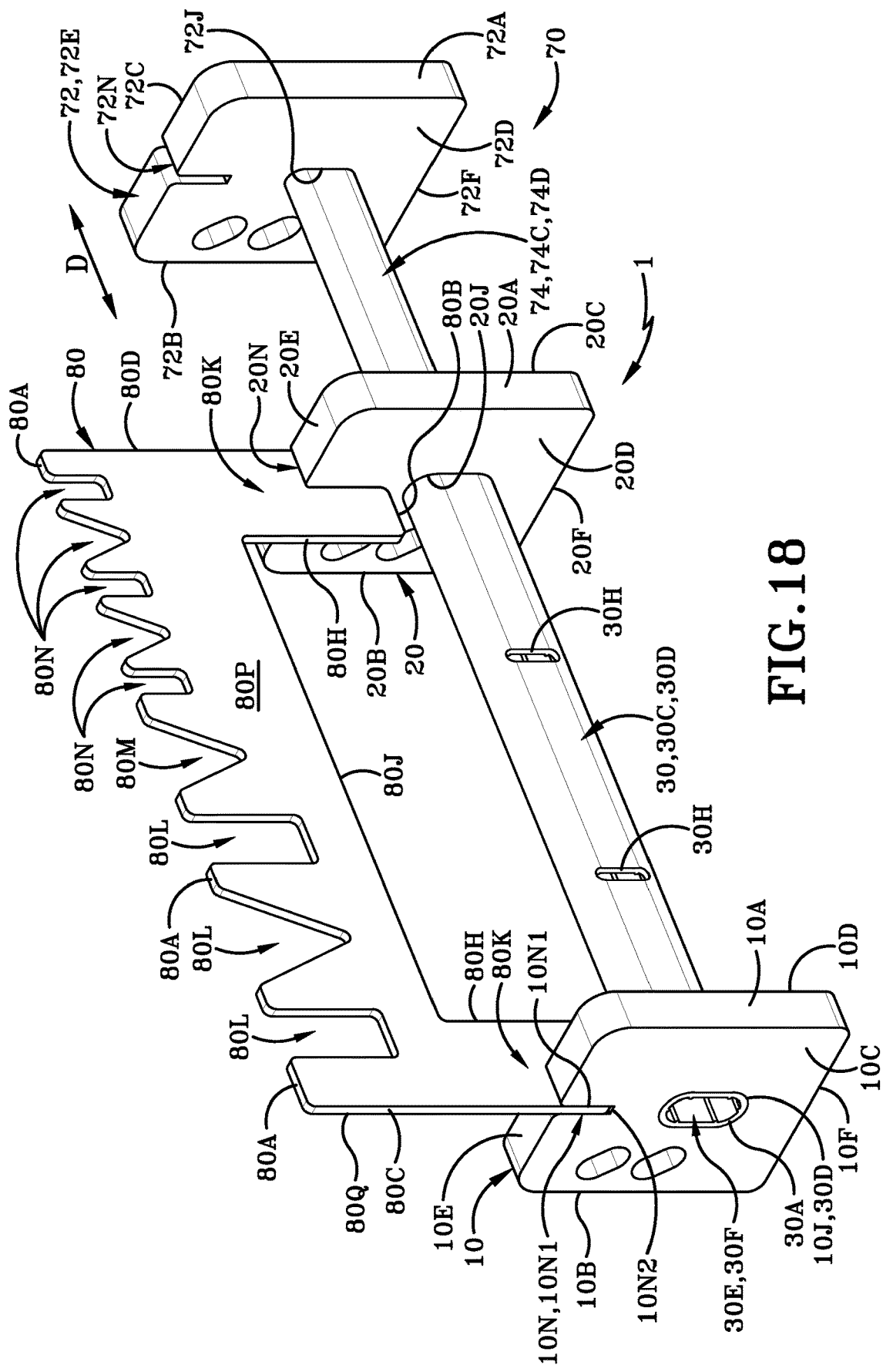
FIG. 18 (FIG. 18) is a front, top, first side isometric perspective view of the surgical instrument stand apparatus shown in FIG. 17, wherein the surgical instrument stand apparatus is equipped with at least one expansion assembly and the second stand accessory.

Rack 80 may also be operably engaged with the expansion assembly 70 if equipped with the stand 1 (see FIG. 18). In this particular embodiment, the rack 80 would be received be the expansion slit 72N of the expansion foot 72 to frictionally fit the rack 80 with the expansion foot 72 once the expansion assembly 70 is set to a desired distance relative to the first foot 10 or the second foot 20.

Figure 17:
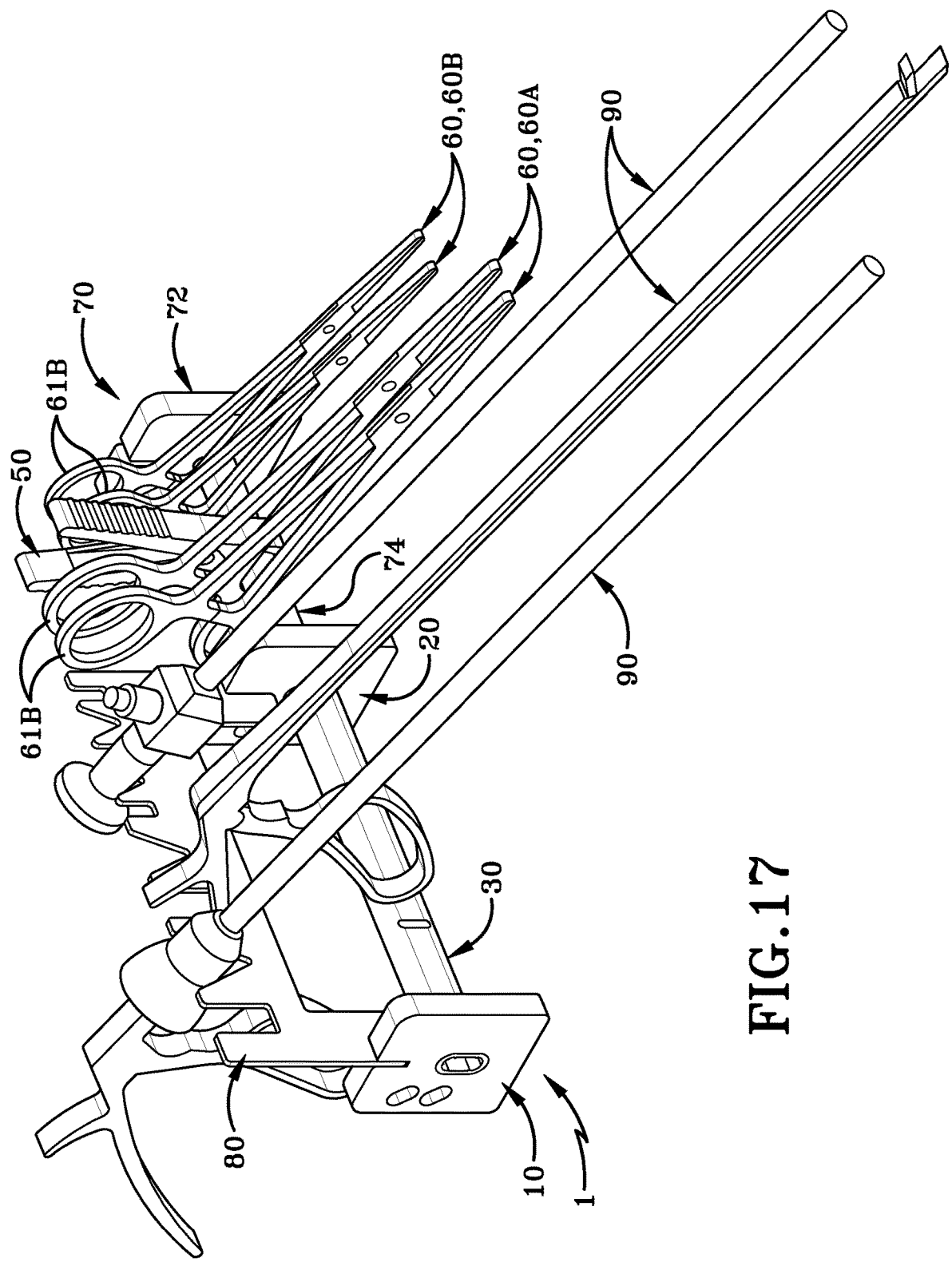
FIG. 17 (FIG. 17) is a front, top, first side isometric perspective view of the surgical instrument stand apparatus in accordance with another aspect of the present disclosure, wherein the set of first surgical instruments is supported with the expansion assembly and at least one clip, and wherein a set of second surgical instruments is supported by a second stand accessory equipped to the surgical instrument stand apparatus.

FIG. 17 illustrates another embodiment of the stand 1 that is equipped with the expansion assembly 70 and the rack 80 to hold both the set of first surgical instruments 60 and the set of second surgical instruments 90 discussed previously. In this embodiment, the set of first surgical instruments 60 would rest on the expansion support bar 74 of the expansion assembly 70 while being separated by a single clip 50. In this same embodiment, the set of second surgical instruments 90 would also rest on the rack 80 inside one or more of the first group of recesses 80L, the second group of recesses 80M, and the third group of recesses 80M. While not illustrated, a user may engage at least one stringer bar 40 with the stand 1, the expansion assembly 70, and the set of first surgical instruments 60 if the user is collectively transporting the stand 1, the expansion assembly 70, and the set of first surgical instruments 60 from an in-queue station to a surgical station or sanitization station.

It should be understood that combination of the stand 1 and the expansion assembly 70 may define any suitable length necessary for transporting and organizing surgical and/or medical equipment. In one exemplary embodiment, a length of combination of a stand and an expansion assembly discussed herein may be approximately six inches long when measured between a first side edge of the plate and a second side edge of the plate. In another exemplary embodiment, another length of a plate of a clamping rack discussed herein may be approximately twelve inches long when measured between a first side edge of the plate and a second side edge of the plate. In yet another exemplary embodiment, another length of a plate of a clamping rack discussed herein may be between six inches up to about twelve inches when measured between a first side edge of the plate and a second side edge of the plate. In yet another exemplary embodiment, another length of a plate of a clamping rack discussed herein may be at least twelve inches when measured between a first side edge of the plate and a second side edge of the plate.

Figure 20:
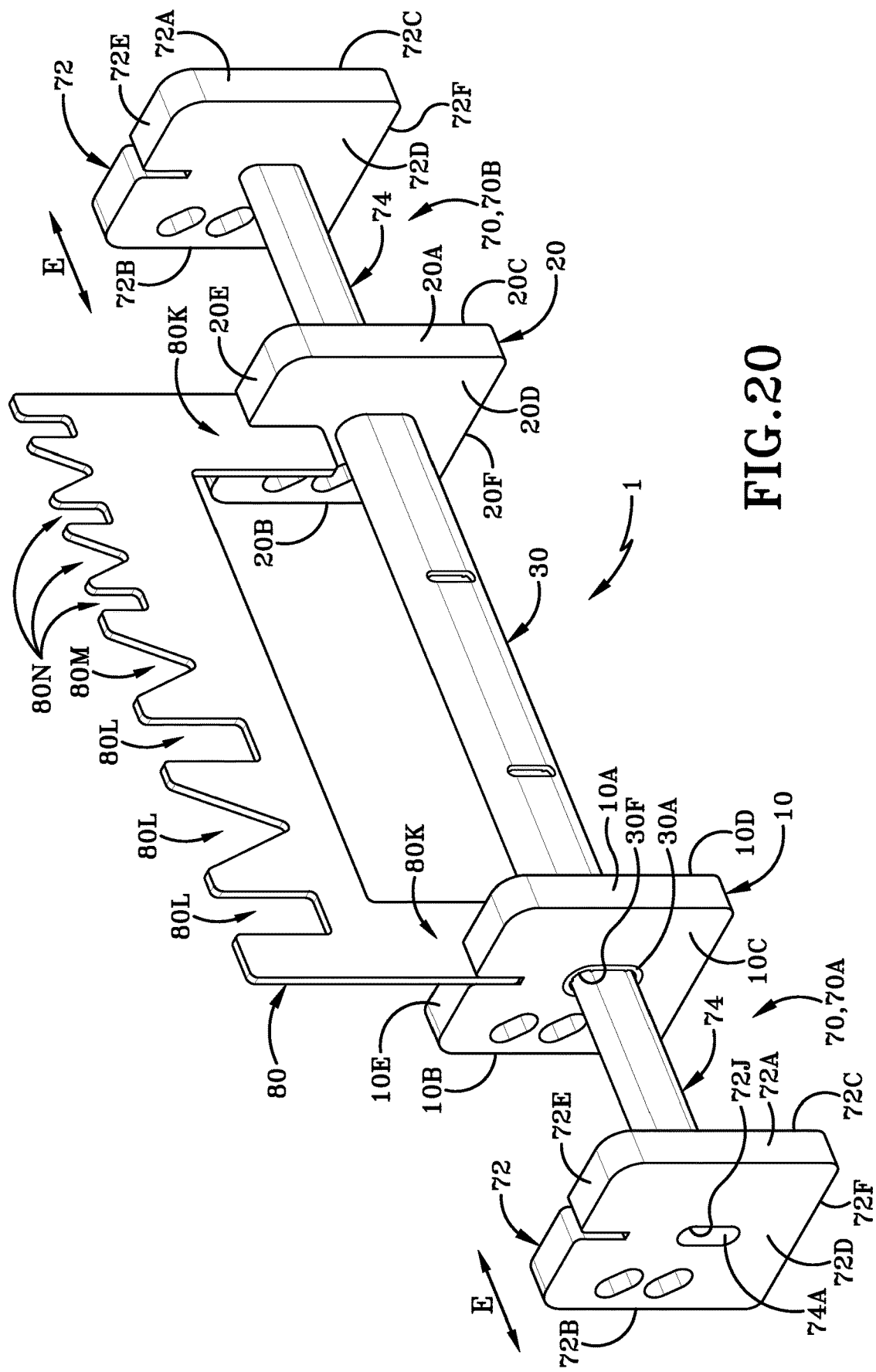
FIG. 20 (FIG. 20) is a front, top, first side isometric perspective view of the surgical instrument stand apparatus in accordance with another aspect of the present disclosure, wherein the surgical instrument stand apparatus is equipped with a first expansion assembly, a second expansion assembly, and the second stand accessory.
Figure 21:
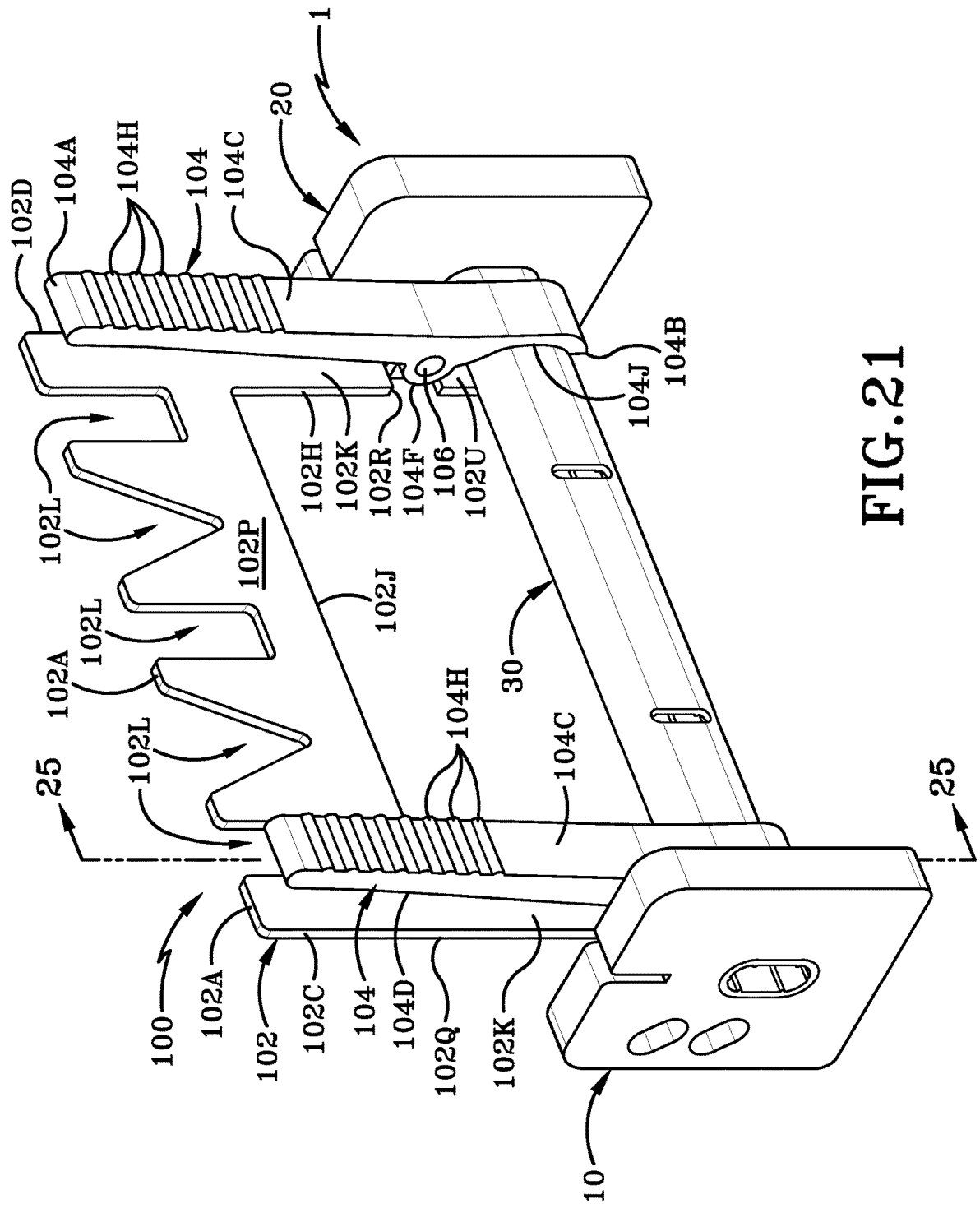
FIG. 21 (FIG. 21) is a front, top, first side isometric perspective view of the surgical instrument stand apparatus in accordance with another aspect of the present disclosure, wherein the surgical instrument stand apparatus is equipped with a clamping rack.

FIG. 20 illustrates another embodiment of the stand 1 that is equipped with a first expansion assembly 70A, a second expansion assembly 70B, and a rack 80. In this particular embodiment, an expansion support bar 74 of the first expansion assembly 70A may be inserted into the support tube 30 at the first end 30A to slidably engage the first expansion assembly 70A with the stand 1. In this same embodiment, an expansion support bar 74 of the second expansion assembly 70B may be inserted into the support tube 30 at the second end 30B to slidably engage the second expansion assembly 70B with the stand 1. Such configuration may be desirable by a user when large amounts of surgical instruments (such as the set of first surgical instruments 60) must be transported for surgical needs or sterilization needs, various types of surgical instrument or devices (such as the set of first surgical instruments 60 and set of second surgical instruments 90) are needed during a single surgical procedure, and other various considerations of the like.

FIGS. 21-25 illustrates another embodiment of the stand 1 that is equipped with at least one clamping rack 100. As discussed in greater detail below, the at least one clamping rack 100 is selectively operably engageable with the support tube 30 between the first foot 10 and the second foot 20. Such features and components of the clamping rack 100 are discussed in greater detail below.

The clamping rack 100 includes a plate 102. In the present disclosure, certain features of the plate 102 of the clamping plate 102 are identical to certain features of the rack 80 mentioned above. As such, a top edge 102A, a bottom edge 102B, a first side edge 102C, a second side edge 102D, a pair of interior vertical edges 102H, a pair of interior horizontal edges 102J, a pair of legs 102K, at least one group of recesses 102L, a front surface 102P, and a rear surface 102Q of the plate 102 of the clamping rack 100 are identical to the top edge 80A, the bottom edge 80B, the first side edge 80C, the second side edge 80D, the pair of interior vertical edges 80H, the pair of interior horizontal edges 80J, the pair of legs 80K, a group of recesses 80L, a front surface 80P, and a rear surface 80Q of the rack 80.

Figure 24:
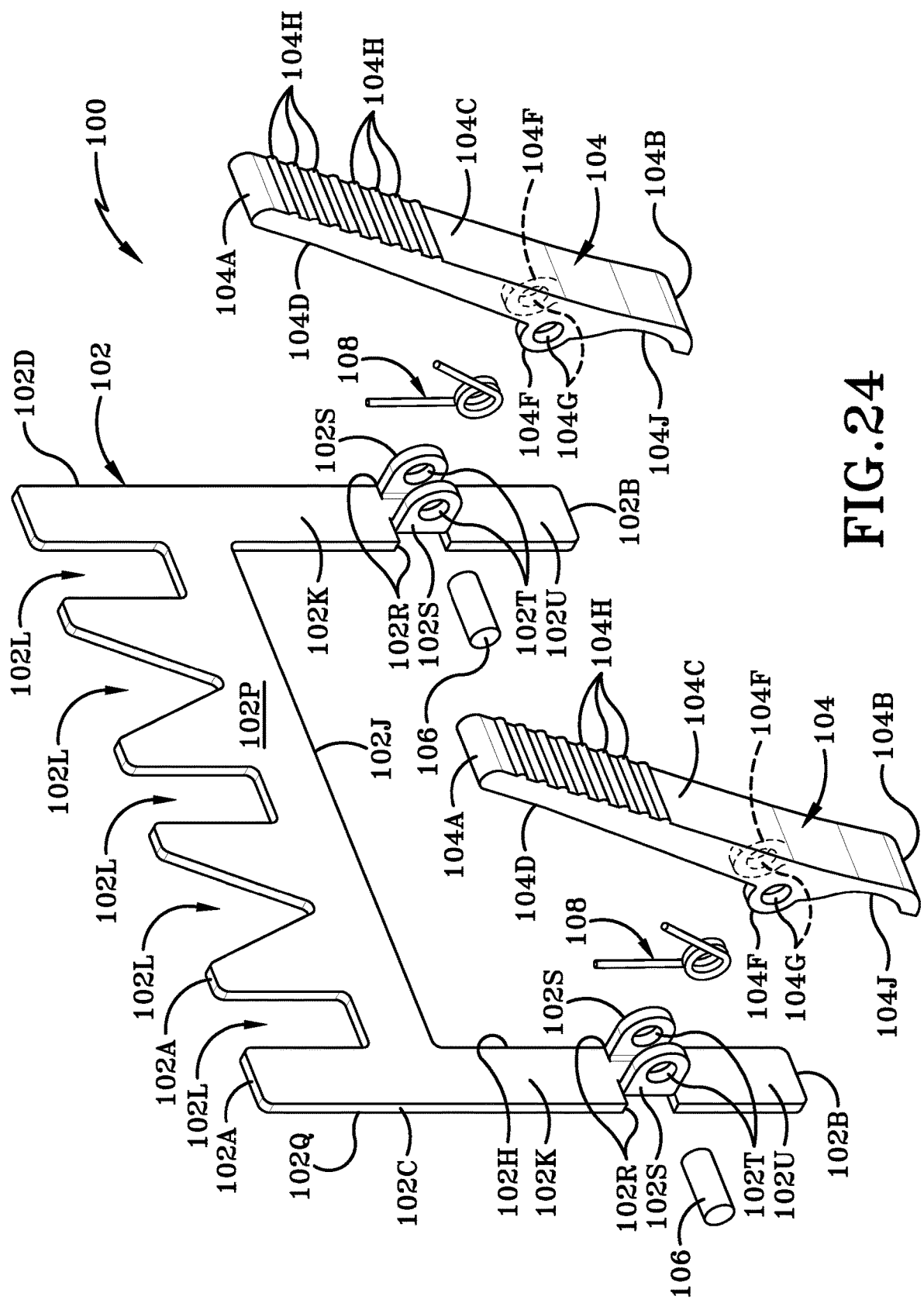
FIG. 24 (FIG. 24) is an exploded view of the clamping rack shown in FIG. 21.

However, the plate 102 of the clamping rack 100 includes different features and/or configurations when compared to the rack 80. As best seen in FIG. 24, the plate 102 includes a pair of cavities 102R that extends into each leg of the pair of legs 102K. In the present disclosure, a first cavity of the pair of cavities 102R extends into each leg of the pair of legs 102K from the first side edge 102C to a respective interior vertical edge of the pair of interior vertical edges 102H. In the present disclosure, a second cavity of the pair of cavities 102R also extends into each leg of the pair of legs 102K from a respective interior vertical edge of the pair of interior vertical edges 102H to the first side edge 102C in which the second cavity of the pair of cavities 102R opposes the first cavity of the pair of cavities 102R. Such use and purpose of the pair of cavities 102R defined in each leg of the pair of legs 102K is discussed in greater detail below.

The plate 102 of the clamping rack 100 also includes a pair of attachment arms 102S that is provided on each leg of the pair of legs 102K. As best seen in FIG. 24, each attachment arm of the pair of attachment arms 102S extends from the respective leg of the pair of legs 102K and is positioned forwardly of the front surface 102P of the plate 102. In one exemplary embodiment, each attachment arm of the pair of attachment arms 102S is bent forwardly from the respective leg of the pair of legs 102K which defines the pair of cavities 102R in each leg of the pair of legs 102K. Each attachment arm of the pair of attachment arms 102S also defines an opening 102T that extends transversely through each attachment arm of the pair of attachment arms 102S. Such use and purpose of the pair of attachment arms 102S provided on each leg of the pair of legs 102K is discussed in greater detail below.

Figure 25:
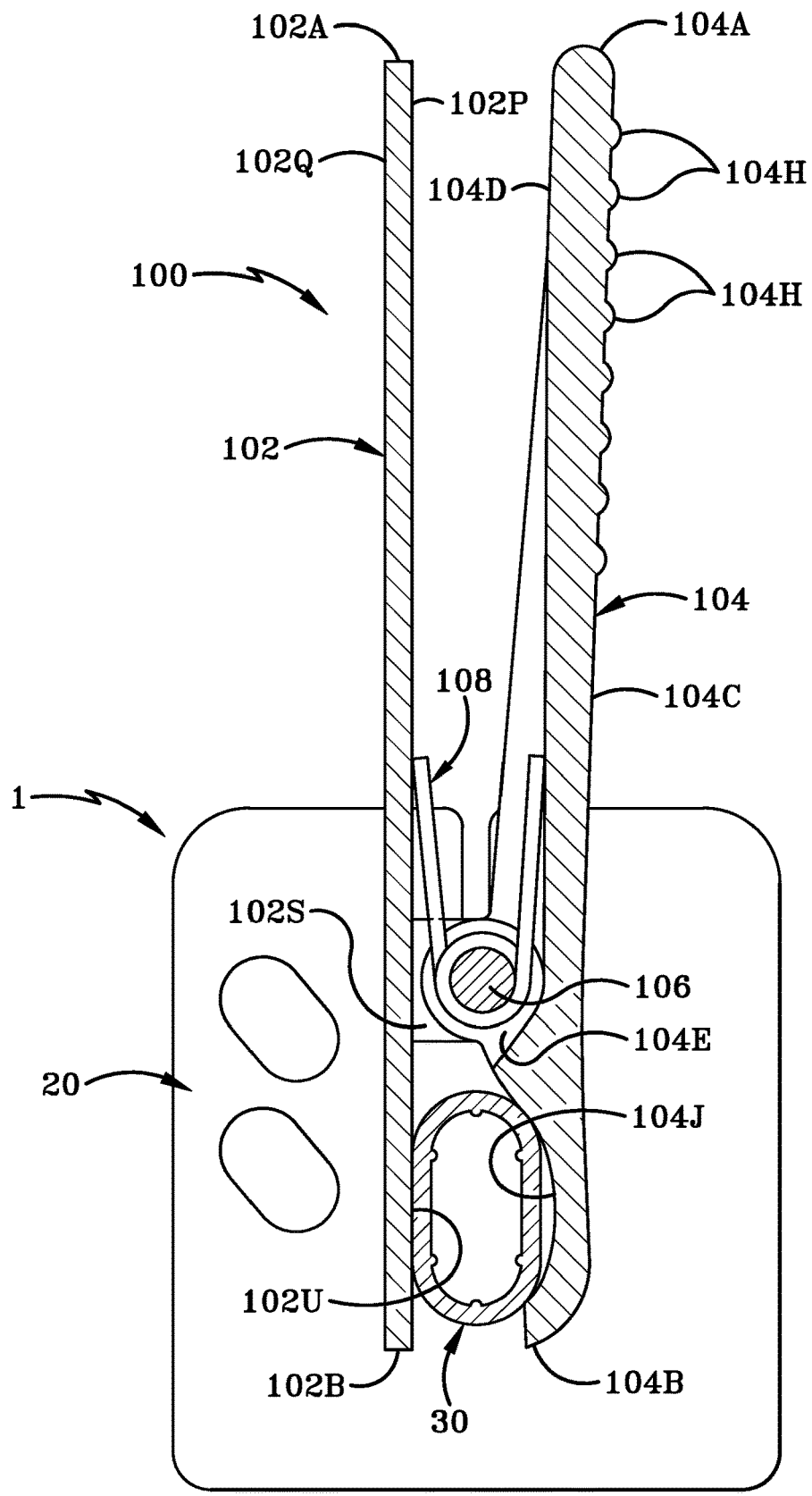
FIG. 25 (FIG. 25) is a sectional view taken in the direction of line 25-25 shown in FIG. 21.

The clamping rack 100 also includes a first clamping surface 102U. As best seen in FIGS. 24 and 25, the first clamping surface 102U is a section of the front surface 102P defined along each leg of the pair of legs 102K. Particularly, the first clamping surface 102U is defined along each leg of the pair of legs 102K between the bottom edge 102B and the pair of attachment arms 102S. In one instance, the first clamping surface 102U engages with the exterior surface 30D of the support tube 30 when the clamping rack 100 engages with the support tube 30. In another instance, the first clamping surface 102U may engage with the exterior surface 74D of the expansion support bar 74 when the clamping rack 100 engages with the expansion support bar 74.

In the present disclosure, the first clamping surface 102U defined along each leg of the pair of legs 102K is planar and/or flat which matches the front surface 102P of the plate 102. In one exemplary embodiment, the first clamping surface 102U defined along each leg of the pair of legs 102K may be curvilinear and/or non-planar. In this exemplary embodiment, the first clamping surface 102U defined along each leg of the pair of legs 102K may match the exterior surface 30D of the support tube 30 and/or the exterior surface 74D of the expansion support bar 74.

It should be understood that the plate 102 of clamping rack 100 may define any suitable length necessary for transporting and organizing surgical and/or medical equipment. In one exemplary embodiment, a length of a plate of a clamping rack discussed herein may be approximately six inches long when measured between a first side edge of the plate and a second side edge of the plate. In another exemplary embodiment, another length of a plate of a clamping rack discussed herein may be approximately twelve inches long when measured between a first side edge of the plate and a second side edge of the plate. In yet another exemplary embodiment, another length of a plate of a clamping rack discussed herein may be between six inches up to about twelve inches when measured between a first side edge of the plate and a second side edge of the plate. In yet another exemplary embodiment, another length of a plate of a clamping rack discussed herein may be at least twelve inches when measured between a first side edge of the plate and a second side edge of the plate.

The clamping rack 100 may also include a set of clips 104 that pivotably engages with the plate 102. As best seen in FIGS. 22-24, each clip of the set of clips 104 includes a top end 104A, a bottom end 104B vertically opposite to the top end 104A, a front surface 104C that extends between top end 104A and the bottom end 104B and faces away from the plate 102, and a rear surface 104D that extends between the top end 104A and the bottom end 104B and faces the plate 102.

Each clip of the set of clips 104 also defines a pair of cavities 104E. As best seen in FIG. 23, the pair of cavities 104E extends forwardly from the rear surface 104D towards the front surface 104C to receive a respective pair of attachment arms 102S of the plate 102 (see FIG. 25). Each clip of the set of clips 104 also includes a pair of attachment extensions 104F that extends rearward from rear surface 104D. Upon assembly of the clamping rack 100, the pair of attachment extensions 104F is positioned internally of a respective pair of attachment arms 102S of the plate 102 to pivotably engage each clip of the set of clips 104 with the plate 102; such pivot engagement is discussed in greater detail below. Each attachment extension of the pair of attachment extensions 104F also defines an opening 104G that extends transversely through each attachment extension of the pair of attachment extension 104G. Such use and purpose of the pair of attachment extensions 104E provided on each clip 104 is discussed in greater detail below.

Each clip of set of clips 104 also defines a grip 104H. As best seen in FIGS. 21-25, the grip 104H is defined along the front surface 104C of each clip of the set of clips 104 at the top end 104A. In the present disclosure, the grip 104H is a plurality of ridges and/or bumps that extends upward from the front surface 104C. In other exemplary embodiments, grip 104H may be defined by any suitable members and/or features on each clip of the set of clips 104.

Each clip of the set of clips 104 also includes a second clamping surface 104J. As best seen in FIGS. 23-25, the second clamping surface 104J is a section of the rear surface 104D defined along each clip of the set of clips 104. Particularly, the second clamping surface 104J of each clip 104 is defined between the bottom end 104B and the pair of attachment extensions 104F. In one instance, the second clamping surface 104J engages with the exterior surface 30D of the support tube 30 when the clamping rack 100 engages with the support tube 30. In another instance, the second clamping surface 104J may engage with the exterior surface 74D of the expansion support bar 74 when the clamping rack 100 engages with the expansion support bar 74. In the present disclosure, the second clamping surface 104J of each clip of the set of clips 104 also defines a curvilinear shape when viewed from a sectional view such that the second clamping surface 104J matches with the exterior surface 30D of the support tube 30 and the exterior surface 74D of the expansion support bar 74 (see FIG. 25).

In other exemplary embodiments, the second clamping surface 104J of each clip of the set of clips 104 may include additional features and/or components to prevent axial rotational of the clamping rack 100 when engaged with the support tube 30 or the expansion support rod 74. In one exemplary embodiment, a set of teeth may be defined along the second clamping surface 104J of each clip of the set of clips 104. Such inclusion of the set of teeth provides additional grip between each clip of the set of clips 104 and one of the support tube 30 and the expansion support bar 74.

While not illustrated herein, each clip of the set of clips 104 may define a through-hole that extends between the front surface 104C and the second clamping surface 104J. Such inclusion of a through-hole in each clip of the set of clips 104 may allow fluid to pass through the respective clip 104 when the clamping rack 100 is being cleaned and remains engaged with the stand 1 or the expansion assembly 70. It should also be understood that a through-hole may also be include in other clips and similar clamping devices mentioned herein.

Clamp assembly 100 also includes pivot pin 106 that pivotably engages the plate 102 and the clips 104 with one another. As best seen in FIG. 25, the pivot pin 106 operably engages with the pairs of attachment arms 102S inside of the openings 102T and with the pairs of attachment extensions 104F inside of the openings 104G. In the present disclosure, the plate 102 and/or clip 104 rotates about the pivot pin 106 so that the clamping rack 100 may be selectively engaged with the support tube 30 or at least one extension support bar 74.

Still referring to FIG. 25, clamping assembly 100 also includes a biaser 108 that operably engages between the plate 102 and a clip of the set of clips 104. In the present disclosure, the biaser 108 is configured to apply an inward force on the plate 102 and the respective clip 104 such that the first clamping surface 102U of the plate 102 and the second clamping surface 104J of the respective clip 104 are biased towards one another. Such configuration of each biaser 108 enables the plate 102 and the set of clips 104 to apply a constant inward pressure towards one another so that the clamping rack 100 remains engaged with the support tube 30 or the extension support bar 74.

It should be understood that any suitable components and/or mechanism may be used to pivotably engage the plate 102 and the clips 104 with one another. In one exemplary embodiment, a fastener and a rivet nut may be provided to pivotably engage the plate 102 and the clips 104 with one another. In this exemplary embodiment, the plate 102 and/or clip 104 rotates about the rivet nut so that the clamping rack 100 may be selectively engaged with the support tube 30 or at least one extension support bar 74. It should be understood that any suitable biaser or biasing means may be used herein to apply an inward force on the plate 102 and the respective clip 104 such that the first clamping surface 102U of the plate 102 and the second clamping surface 104J of the respective clip 104 are biased towards one another. In one exemplary embodiment, a torsion spring operably engages with the plate 102 and a respective clip of the set of clips 104 that applies an inward force on the plate 102 and the respective clip 104 such that the first clamping surface 102U of the plate 102 and the second clamping surface 104J of the respective clip 104 are biased towards one another.

Figure 26:
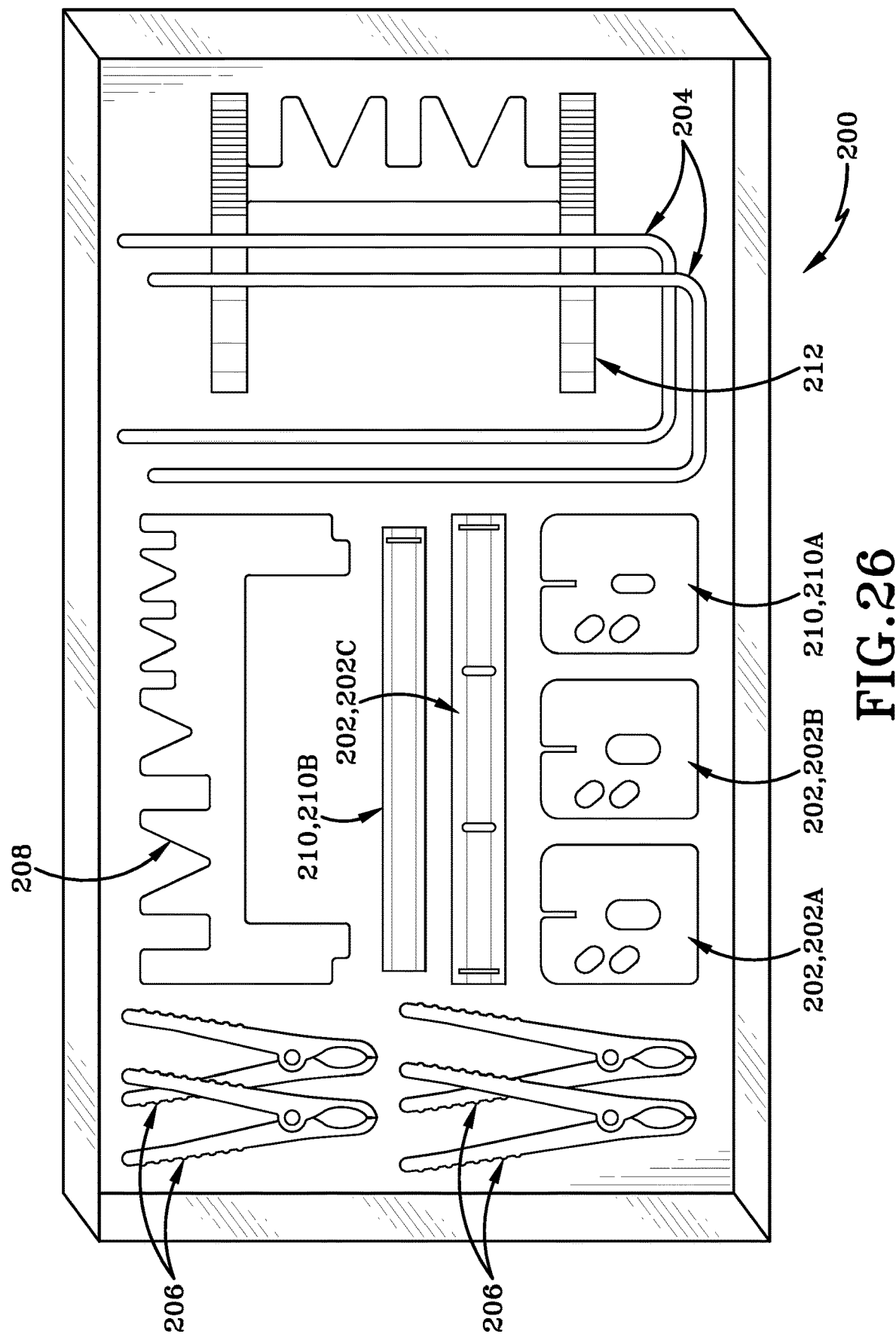
FIG. 26 (FIG. 26) is an exemplary kit of the surgical instrument stand apparatus, a set of clips, a pair of first stand accessories, and at least one second stand accessory.

FIG. 26 illustrates a kit 200. In the illustrated embodiment, kit 200 may include various components and/or accessories that are mentioned herein. In the present embodiment, the kit 200 may include components of a stand 202, particularly a first foot 202A (e.g., first foot 10 of stand 1), a second foot 202B (e.g., second foot 20 of stand 1), and support tube 202C (e.g., support tube 30 of stand 1). The kit 200 may also include at least two or more stringer bars 204 (e.g., stringer bars 40) and a plurality of clips 206 (e.g., clips 50). The kit 200 may also include a rack 208 (e.g., rack 80) and at least one expansion assembly 110, particularly an expansion foot 210A (e.g., expansion foot 72 of expansion assembly 70) and an expansion support rod 210B (e.g., expansion support bar 74 of expansion assembly 70). The kit 200 may also include a clamping rack 212 (e.g., clamping rack 100) that is discussed and illustrated herein. It should be understood that kit 200 may include alternative components that are discussed herein as well as additional components that are currently included in kit 200.

Figure 27:
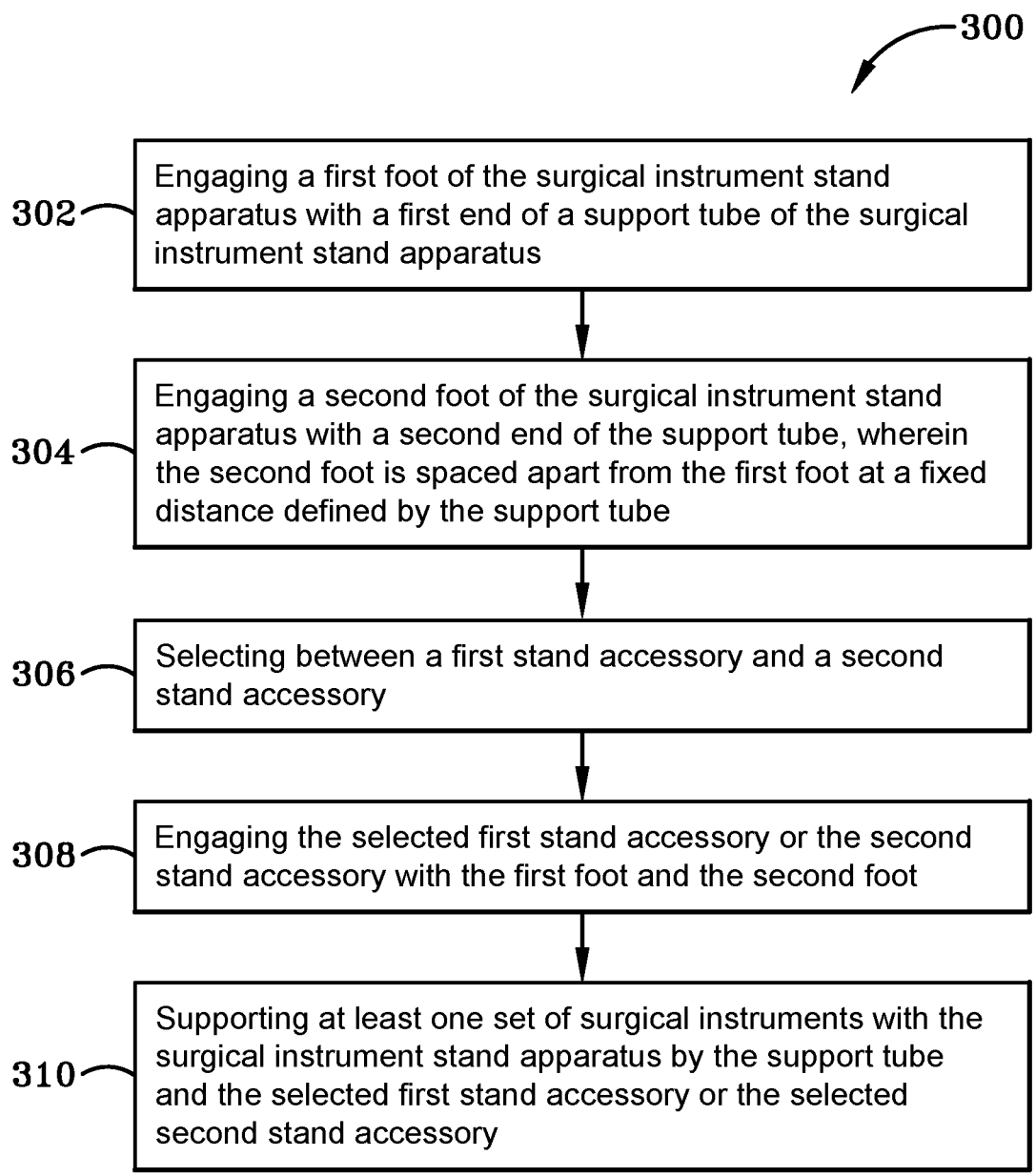
FIG. 27 (FIG. 27) is an exemplary method flowchart.

FIG. 27 illustrates a method 300 of supporting at least one set of surgical instruments with a surgical instrument stand apparatus. An initial step 302 of method 300 includes engaging a first foot of the surgical instrument stand apparatus with a first end of a support tube of the surgical instrument stand apparatus. Another step 304 of method 300 includes engaging a second foot of the surgical instrument stand apparatus with a second end of the support tube, wherein the second foot is spaced apart from the first foot at a fixed distance defined by the support tube. Another step 306 of method 300 includes selecting between a first stand accessory and a second stand accessory. Another step 308 of method 300 includes engaging the selected first stand accessory or the second stand accessory with the first foot and the second foot. Another step 210 of method 300 includes supporting at least one set of surgical instruments with the surgical instrument stand apparatus by the support tube and the selected first stand accessory or the selected second stand accessory.

In other exemplary embodiments, method 300 may include additional and/or optional steps. In one exemplary embodiment, method 300 may include that when the first stand accessory is selected, the method further comprises: inserting a first end of the first stand accessory through the first foot, the second foot, and first handles of the at least one set of surgical instruments; engaging the first stand accessory with the first foot, the second foot, and the first handles of the at least one set of surgical instruments; inserting a second end of the first stand accessory through second handles of the at least one set of surgical instruments; and engaging the first stand accessory with the second handles of the at least one set of surgical instruments. In another exemplary embodiment, method 300 may include steps of clamping at least one clip with the support tube; and separating the at least one set of surgical instruments into at least two groups. In another exemplary embodiment, method 300 may include that when the second stand accessory is selected in the step of selecting between the first stand accessory and the second stand accessory, the method further comprises: engaging a first end of the second stand accessory with the first foot inside a first slit defined in the first foot; and engaging a second end of the second stand accessory with the second foot inside a second slit defined in the second foot; wherein the second stand accessory is positioned above and spaced apart from the support tube. In another exemplary embodiment, method 300 may include steps of engaging at least one expansion assembly with the support tube at one or both of the first end of the support tube and the second end of the support tube. In another exemplary embodiment, method 300 may include that when the second stand accessory is selected in the step of selecting between the first stand accessory and the second stand accessory, the method further comprises: engaging a first end of the second stand accessory with one of the first foot inside a first slit defined in the first foot and the second foot inside a second slit defined in the second foot; and engaging a second end of the second stand accessory with an expansion foot of the expansion assembly inside an expansion slit defined in the expansion foot; wherein the second stand accessory is positioned above and spaced apart from the support tube and an expansion support bar of the expansion assembly.

It should be understood that the term "stand accessory" or similar terms used herein may be any accessory that is capable and/or equipped to support and/or organize one or more sets of surgical instruments on the stand 1 or at least one expansion assembly 70. In one instance, a stand accessory may be stringer bar 40 that is capable of supporting and/or organizing one or more sets of surgical instruments on the stand 1 or at least one expansion assembly 70. In another instance, a stand accessory may also be racks 80, 80' that is capable of supporting and/or organizing one or more sets of surgical instruments on the stand 1 or at least one expansion assembly 70. In yet another instance, a stand accessory may clamping rack 100 that is capable of supporting and/or organizing one or more sets of surgical instruments on the stand 1 or at least one expansion assembly 70.

Various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The articles "a" and "an," as used herein in the specification and in the claims, unless clearly indicated to the contrary, should be understood to mean "at least one." The phrase "and/or," as used herein in the specification and in the claims (if at all), should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

While components of the present disclosure are described herein in relation to each other, it is possible for one of the components disclosed herein to include inventive subject matter, if claimed alone or used alone. In keeping with the above example, if the disclosed embodiments teach the features of A and B, then there may be inventive subject matter in the combination of A and B, A alone, or B alone, unless otherwise stated herein.

As used herein in the specification and in the claims, the term "effecting" or a phrase or claim element beginning with the term "effecting" should be understood to mean to cause something to happen or to bring something about. For example, effecting an event to occur may be caused by actions of a first party even though a second party actually performed the event or had the event occur to the second party. Stated otherwise, effecting refers to one party giving another party the tools, objects, or resources to cause an event to occur. Thus, in this example a claim element of "effecting an event to occur" would mean that a first party is giving a second party the tools or resources needed for the second party to perform the event, however the affirmative single action is the responsibility of the first party to provide the tools or resources to cause said event to occur.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Spatially relative terms, such as "under", "below", "lower", "over", "upper", "above", "behind", "in front of", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal", "lateral", "transverse", "longitudinal", and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed herein could be termed a second feature/element, and similarly, a second feature/element discussed herein could be termed a first feature/element without departing from the teachings of the present invention.

An embodiment is an implementation or example of the present disclosure. Reference in the specification to "an embodiment," "one embodiment," "some embodiments," "one particular embodiment," "an exemplary embodiment," or "other embodiments," or the like, means that a particular feature, structure, or characteristic described in connection with the embodiments is included in at least some embodiments, but not necessarily all embodiments, of the invention. The various appearances "an embodiment," "one embodiment," "some embodiments," "one particular embodiment," "an exemplary embodiment," or "other embodiments," or the like, are not necessarily all referring to the same embodiments.

If this specification states a component, feature, structure, or characteristic "may", "might", or "could" be included, that particular component, feature, structure, or characteristic is not required to be included. If the specification or claim refers to "a" or "an" element, that does not mean there is only one of the element. If the specification or claims refer to "an additional" element, that does not preclude there being more than one of the additional element.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Additionally, the method of performing the present disclosure may occur in a sequence different than those described herein. Accordingly, no sequence of the method should be read as a limitation unless explicitly stated. It is recognizable that performing some of the steps of the method in a different order could achieve a similar result.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

To the extent that the present disclosure has utilized the term "invention" in various titles or sections of this specification, this term was included as required by the formatting requirements of word document submissions pursuant the guidelines/requirements of the United States Patent and Trademark Office and shall not, in any manner, be considered a disavowal of any subject matter.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of various embodiments of the disclosure are examples and the disclosure is not limited to the exact details shown or described.

What is claimed is:

1. A surgical instrument stand apparatus, comprising:
   a first foot;
   a second foot;
   a support tube extending between the first foot and the second foot and being a unitary, monolithic member, the support tube having a first end operably engaging with the first foot, a second end longitudinally opposite to the first end and operably engaging with the second foot, and a fixed length measured between the first end and the second end, wherein the first foot and the second foot are held at a fixed distance from one another by the support tube; and
   at least one stand accessory selectively operably engageable with the first foot and the second foot for supporting at least one set of surgical instruments.

2. The surgical instrument stand apparatus of claim 1, wherein when the at least one set of surgical instruments is supported by the at least one stand accessory, the at least one stand accessory is engaged with the first foot and the second foot at first positions.

3. The apparatus of claim 1, wherein each of the first foot and the second foot comprises:
   an outer side;
   an inner side facing in an opposite direction relative to the outer side;
   a central opening extending between the outer side and the inner side and configured to receive the support tube; and
   at least two accessory openings extending between the outer side and the inner side and being offset from the central opening; and
   wherein one of the at least two accessory openings is configured to receive the at least one stand accessory; and
   wherein the at least two accessory openings of the first foot and the second foot define diameters that are equal to one another.

4. The apparatus of claim 1, wherein the support tube further comprises:
   a wall extending between the first end and the second end and defining a passageway therethrough with an inner diameter.

5. The apparatus of claim 4, wherein the support tube further comprises:
   at least one opening defined in the wall between the first end of the support tube and the second end of the support tube;
   wherein the at least one opening provides fluid communication between the passageway of the support tube and an external environment that surrounds the support tube.

6. The apparatus of claim 4, further comprising:
   an expansion assembly selectively operably engagable with the support tube at one of the first end of the support tube and the second end of the support tube.

7. The apparatus of claim 6, wherein the expansion assembly comprises:
   an expansion foot; and
   an expansion support bar extending between the expansion foot and one of the first foot and the second foot.

8. The apparatus of claim 7, wherein the expansion support bar comprises:
   a first end that operably engages with the expansion foot;
   a second end that is longitudinally opposite to the first end and is configured to selectively operably engage with the support tube at one of the first end of the support tube and the second end of the support tube; and
   a wall extending between the first end and the second end and defining an outer diameter that is less than the inner diameter of the support tube;
   wherein the expansion support bar is slidably moveably inside of the passageway of the support tube.

9. The apparatus of claim 1, further comprising:
   at least one clip that is selectively operably engageable with the support tube;
   wherein the at least one clip is selectively positionable along the support tube between the first foot and the second foot, wherein the at least one clip is configured to separate one surgical instrument of the at least one set of surgical instruments from another surgical instrument of the at least one set of surgical instruments.

* * * * *